(12) United States Patent
Valtakari et al.

(10) Patent No.: US 7,256,032 B2
(45) Date of Patent: Aug. 14, 2007

(54) ENZYMES

(75) Inventors: Leena Valtakari, Rajamäki (FI); Marika Alapuranen, Tuusula (FI); Satu Hooman, Espoo (FI); Matti Siika-Aho, Helsinki (FI); Jarno Kallio, Järvenpää (FI); Liisa Viikari, Helsinki (FI); Pentti Ojapalo, Tuusula (FI); Jari Vehmaanperä, Klaukkala (FI)

(73) Assignee: AB Enzymes Oy, Rajamaki (FI)

( * ) Notice: Subject to any disclaimer, the term of this patent is extended or adjusted under 35 U.S.C. 154(b) by 0 days.

(21) Appl. No.: 11/316,397

(22) Filed: Dec. 22, 2005

(65) Prior Publication Data
US 2007/0148732 A1 Jun. 28, 2007

(51) Int. Cl.
*C12N 9/42* (2006.01)
*C12N 1/00* (2006.01)
*C12N 1/20* (2006.01)
*C12P 21/06* (2006.01)
*C12P 19/34* (2006.01)
*D07H 21/02* (2006.01)
*C07H 21/02* (2006.01)

(52) U.S. Cl. ............ 435/209; 435/69.1; 435/91.1; 435/252.3; 435/254.11; 435/263; 435/264; 435/277; 426/20; 426/21; 536/23.1; 536/23.2; 510/226; 510/300; 510/320

(58) Field of Classification Search .......... 435/209, 435/69.1, 263; 510/515
See application file for complete search history.

(56) References Cited

U.S. PATENT DOCUMENTS

| | | | |
|---|---|---|---|
| 3,664,961 A | 5/1972 | Norris | 252/99 |
| 5,433,750 A | 7/1995 | Gradinger et al. | 623/16 |
| 5,770,418 A | 6/1998 | Yaver et al. | 435/189 |
| 5,843,745 A | 12/1998 | Berka et al. | 435/189 |
| 5,874,293 A | 2/1999 | Miettinen-Oinonen et al. | 435/263 |
| 5,948,672 A | 9/1999 | Rasmussen et al. | 435/264 |
| 5,958,082 A * | 9/1999 | Lund et al. | 8/102 |
| 6,001,639 A * | 12/1999 | Schulein et al. | 435/263 |
| 6,387,690 B1 * | 5/2002 | Schulein et al. | 435/263 |
| 6,573,086 B1 | 6/2003 | Emalfrab et al. | 435/254.11 |
| 6,855,531 B2 * | 2/2005 | Shulein et al. | 435/209 |
| 2002/0168751 A1 | 11/2002 | Mettinen-Oinonen et al. | 435/209 |

FOREIGN PATENT DOCUMENTS

| | | |
|---|---|---|
| EP | 0 238 216 | 9/1987 |
| EP | 0 244 234 | 11/1987 |
| EP | 0 495 258 | 7/1992 |
| EP | 0 843 041 | 5/1997 |
| EP | 1 291 431 | 3/2003 |
| WO | WO 94/07998 | 4/1994 |
| WO | WO 95/33386 | 12/1995 |
| WO | WO 96/29397 | 9/1996 |
| WO | WO 97/08325 | 3/1997 |
| WO | WO 98/12307 | 3/1998 |
| WO | WO 00/20555 | 4/2000 |
| WO | WO 04/053039 | 6/2004 |

OTHER PUBLICATIONS

Altschul et al., "Basic Local Alignment Search Tool," *J. Mol. Biol.* 215:403-410 (1990).

Bailey and Nevalainen, "Induction, isolation and testing of stable *Trichoderma reesei* mutants with improved production of solubilizing cellulose," *Enz. Microbiol. Technol.* 3:153-157 (1981).

Bendtsen et al., "Improved Prediction of Signal Peptides: SignalP 3.0," *J. Mol. Biol.* 340:783-795 (2004).

Gasteiger et al., "ExPASy: the proteiomics server for in-depth protein knowledge and analysis," *Nucleic Acids Res.* 31(13):3784-3788 (2003).

Ghose, "Measurement of Cellulase Activites," International Union of Pure and Applied Chemistry, *Pure & Application. Chem.*, 59(2):257-268 (1987).

Gupta et al., "Prediction of N-glycosylation sites in human proteins, using artificial neural networks that the sequence context of Asn-Xaa-Ser/Thr sequons.," www.cbs.dtu.dk/services/NetNGlyc/ (2004).

Haakana et al., "Cloning of cellulase genes from *Melanocarpus albomyces* and their efficient expression in *Trichoderma reesei*," *Enz. Microbiol. Technol.* 34:159-167 (2004).

Henrissat, "A classification of glycosyl hydrolases based on amino acid sequence similarities," *Biochem. J.* 280:309-316 (1991).

Henrissat and Bairoch ,"New families in the classification of glycosyl hydrolases based on amino acid sequence similarities," *Biochem. J.* 293:781-788 (1993).

Henrissat and Bairoch "Updating the sequence-based classification of glycosyl hydrolases," *Biochem. J.* 316:695-696 (1996).

Joutsjoki et al., "Transformation of *Trichoderma reesei* with the *Hormoconis resinae* glucoamylase P (*gamP*) gene: production of a heterologous glucoamylase by *Trichoderma reesei*," *Curr. Genet.* 24:223-228 (1993).

Karhunen et al., "High frequency one-step gene replacement in *Trichoderma reesei*. I. Endoglucanase I overproduction," *Mol. Gen. Genet.* 241:515-522 (1993).

Lowry et al., "Protein measurement with the Folin phenol reagent," *J. Biol Chem* 193:265-275 (1951).

(Continued)

*Primary Examiner*—Rebecca E. Prouty
*Assistant Examiner*—Ganapathirama Raghu
(74) *Attorney, Agent, or Firm*—Banner & Witcoff, Ltd.

(57) ABSTRACT

The present invention relates to novel cellulase enzymes, especially novel endoglucanases including endoglucanase fusion proteins, preparations and compositions containing these endoglucanase enzymes and fusion proteins, expression vectors, host cells and methods for their preparation and uses of the cellulases, preparations and compositions in the textile, detergent and pulp and paper industries.

21 Claims, 4 Drawing Sheets

OTHER PUBLICATIONS

Malardier et al., "Cloning of the nitrate reductase gene (niaD) of Aspergillus nidulans and its use for transformation of Fusarium oxysporum," *Gene* 78:147-156 (1989).

Needleman and Wunsch "A General Method Applicable to the Search for Similarities in the Amino Acid Sequence of Two Proteins," *J. Mol. Biol.* 48:443-453 (1970).

Nielsen et al., "Identification of prokaryotic and eukaryotic signal peptides and prediction of their cleavage sites," *Prot. Engineering* 10(1):1-6 (1997).

Nierstrasz and Warmoeskerken "Process engineering and inustrial enzyme applications," *Textile Processing with Enzymes.* A. Cavaco-Paulo and G.M. Gübitz (eds.) Woodhead Publishing Ltd, Cambridge. pp. 120-157 (2003).

Paloheimo et al., "High-Yield Production of a Bacterial Xylanase in the Filamentous Fungus *Trichoderma reesei* Requires a Carrier Polypeptide with an Intact Domain Structure," *Appl. Env. Microbiol.* 69(12):7073-7082 (2003).

Penttilä et al. "A versatile transformation system for the cellulolytic filamentous fungus *Trichoderma reesei,*" *Gene* 61:155-164 (1987).

Raeder and Broda, "Rapid preparation of DNA from filamentous fungi," *Lett. Appl. Microbiol.* 1:17-20 (1985).

Rice et al., "EMBOSS: The European Molecular Biology Open Software Suite," *Trends in Genetics* 16(6):276-277 (2000).

Ward et al., "Cloning Sequence and Preliminary Structural Analysis of a Small, High pI Endoglucanase (EGIII) from *Trichoderma reesei,*" *Proceedings of the second TRICEL symposium on Trichoderma reesei Cellualses and other Hydrolases*, Espoo, Finland, 1993, P. Suominen and T. Reinikainen eds., Foundation for Biotechnical and Industrial Fermentation Research 8 (1993):153-158 (1993).

GenBank Accession No. AJ515703.
GenBank Accession No. AR094305.
GenBank Accession No. CQ827970.
English abstract of WO 95/33386.

Kikuchi et al., Database EMBL-EBI: "Beta-1, 4-endoglucanase precursor," Database accession No. Q6BCL3_BURXY (2004).

Murashima et al., Database EMBL-EBI: "Endoglucanase enzyme NCE5 and cellulase preparation containing the same," Database accession No. BD541138 & WO 01/90375 A1 (2002).

Nakane et al., Database EMBL-EBI: "Endoglucanase STCE and cellulase preparation containing thereof," Database accession No. BD83858 & WO 2005/054475 A1 (2005).

Nakatani et al., Database EMBL-EBI: "Cellulase (EC 3.2.1.4)," Database accession No. Q7M4T4_9PEZI (2003).

Okakura et al., Database EMBL-EBI: "Novel detergent resistant cellulase," Database accession No. BD755354& WO 2004/039969 A1 (2004).

Takashima et al., Database EMBL-EBI: "Endoglucanase," Database accession No. 093783_HUMGT (1999).

Kim et al., "Functional Analysis of a Hybrid Endoglucanase of Bacterial Origin Having a Cellulose Binding Domain from a Fungal Exoglucanase," *Appl. Biochem. and Biotech.*, 75:193-204 (1998).

Poole et al., "Characterization of hybrid proteins consisting of the catalytic domains of *Clostridium* and *Ruminococcus* endoglucanases, fused to *Pseudomonas* non-catalytic cellulose-binding domains," *Biochem., J.*, 279:787-792 (1991).

Takashima et al., "Comparison of gene structures and enzymatic properties between two endoglucanases from *Humicola grisea,*" *J. Biotech.*, 67:85-97 (1999).

\* cited by examiner

SEQUENCE LISTING

<160> NUMBER OF SEQ ID NOS: 21

<210> SEQ ID NO 1
<211> LENGTH: 2334
<212> TYPE: DNA
<213> ORGANISM: Acremonium thermophilum
<220> FEATURE:
<221> NAME/KEY: CDS
<222> LOCATION: (715)...(797)
<220> FEATURE:
<221> NAME/KEY: intron
<222> LOCATION: (798)...(856)
<220> FEATURE:
<221> NAME/KEY: CDS
<222> LOCATION: (857)...(1105)
<220> FEATURE:
<221> NAME/KEY: intron
<222> LOCATION: (1106)...(1228)
<220> FEATURE:
<221> NAME/KEY: CDS
<222> LOCATION: (1229)...(1787)
<220> FEATURE:
<221> NAME/KEY: misc_feature
<222> LOCATION: 13
<223> OTHER INFORMATION: n = A,T,C or G

<400> SEQUENCE: 1

```
tctgtctctt gtntcagaac agatctcctg gcggcctgct ttgccggtcc gaattgcgat      60
cgatgcaacg tcgattgcat acgagctaag cccgtctcgt gataaccgca agggtcttc     120 cgagtttctg tctgcgaccc aggcattttc cgatttgtgt gcggggaccc aactgtcttc     180
tggggagtac ctggtgacaa agcacagat aaacagatgg atgacggtat tgctgtgata     240
tcgccgtggc gctgaatcct ttctcttcgc taccaagata tttattcccc gttgtgaaat     300
cttctattca gcccatccca tccggcaaca cgcatctgct tttcgttccg gcattccgat     360
acctggttcc tggagtgcct accgagcctc gcttcctggg atcgggcgtt gcaccccgcc     420
aaaccctatg ccccaaacgg tacggacaag gatgccggac cccggttttg tccagaaagg     480
ttgcattcct acccacctcg ctggagccac aacatgcaga tcaccgcccg agggaggaca     540
tgtgtggtgc agggacgttg gcaactctgc tgtgtctgaa gtatatgagg ccgatggttc     600
tccttgcaca aagcagagaa tggagtagcc agctcctcct caccagagtc gcctttgcag     660
cgtctcggca ttgcaggctc cccatcgtca gcatttcact tctcagcaac gaac atg     717
                                                                 Met
                                                                  1 cgc tcc tca ccc ttt ctc cgc gca gct ctg gct gcc gct ctg cct ctg     765
Arg Ser Ser Pro Phe Leu Arg Ala Ala Leu Ala Ala Ala Leu Pro Leu
             5                  10                  15 agc gcc cat gcc ctc gac gga aag tcg acg ag gtatgccaat cctcgtacct     817
Ser Ala His Ala Leu Asp Gly Lys Ser Thr Arg
         20                  25 ctgccctctg tagaaacaag tgaccgactg caaagacag a tac tgg gac tgc tgc     872
                                            Tyr Trp Asp Cys Cys
                                                 30
```

-continued

| | |
|---|---|
| aag ccg tcc tgc ggc tgg ccg gga aag gcc tcg gtg aac cag ccc gtc<br>Lys Pro Ser Cys Gly Trp Pro Gly Lys Ala Ser Val Asn Gln Pro Val<br>35                        40                       45 | 920 |
| ttc tcg tgc tcg gcc gac tgg cag cgc atc agc gac ttc aac gcg aag<br>Phe Ser Cys Ser Ala Asp Trp Gln Arg Ile Ser Asp Phe Asn Ala Lys<br>50                     55                  60                  65 | 968 |
| tcg ggc tgc gac gga ggc tcc gcc tac tcg tgc gcc gac cag acg ccc<br>Ser Gly Cys Asp Gly Gly Ser Ala Tyr Ser Cys Ala Asp Gln Thr Pro<br>70                  75                  80 | 1016 |
| tgg gcg gtc aac gac aac ttc tcg tac ggc ttc gca gcc acg gcc atc<br>Trp Ala Val Asn Asp Asn Phe Ser Tyr Gly Phe Ala Ala Thr Ala Ile<br>85                     90                  95 | 1064 |
| gcc ggc ggc tcc gag tcc agc tgg tgc tgc gcc tgc tat gc gtgagttctc<br>Ala Gly Gly Ser Glu Ser Ser Trp Cys Cys Ala Cys Tyr Ala<br>100                 105              110 | 1115 |
| tgcaagccgc ttcccacccc cgctttctgt gcaggccgct tccccctac ccacccactt | 1175 |
| cccccccccc gcctctgtga tcgggcatcc gagctaagtt gcgtgtcgtc cag a ctc<br>                                                                        Leu | 1232 |
| acc ttc aac tcg ggc ccc gtc gcg ggc aag acc atg gtg gtg cag tcg<br>Thr Phe Asn Ser Gly Pro Val Ala Gly Lys Thr Met Val Val Gln Ser<br>115                 120              125 | 1280 |
| acc agc acc ggc ggc gac ctg ggc agc aac cag ttc gac ctc gcc atc<br>Thr Ser Thr Gly Gly Asp Leu Gly Ser Asn Gln Phe Asp Leu Ala Ile<br>130                 135              140 | 1328 |
| ccc ggc ggc gtg ggc atc ttc aac ggc tgc gcc tcc cag ttc ggc<br>Pro Gly Gly Val Gly Ile Phe Asn Gly Cys Ala Ser Gln Phe Gly<br>145                    150                  155                  160 | 1376 |
| ggc ctc ccc ggc gcc cag tac ggc ggc atc agc gac cgc agc cag tgc<br>Gly Leu Pro Gly Ala Gln Tyr Gly Gly Ile Ser Asp Arg Ser Gln Cys<br>               165                        170                       175 | 1424 |
| tcg tcc ttc ccc gcg ccg ctc cag ccg ggc tgc cag tgg cgc ttc gac<br>Ser Ser Phe Pro Ala Pro Leu Gln Pro Gly Cys Gln Trp Arg Phe Asp<br>                    180                        185                       190 | 1472 |
| tgg ttc cag aac gcc gac aac ccc acc ttc acc ttc cag cgc gtg cag<br>Trp Phe Gln Asn Ala Asp Asn Pro Thr Phe Thr Phe Gln Arg Val Gln<br>               195                       200                     205 | 1520 |
| tgc ccg tcc gag ctc acg tcc cgc acg ggc tgt aag cgc gac gac gac<br>Cys Pro Ser Glu Leu Thr Ser Arg Thr Gly Cys Lys Arg Asp Asp Asp<br>210                 215              220 | 1568 |
| gcc agc tat ccc gtc ttc aac ccg cct agc ggt ggc tcc ccc agc acc<br>Ala Ser Tyr Pro Val Phe Asn Pro Pro Ser Gly Gly Ser Pro Ser Thr<br>225                    230                  235                  240 | 1616 |
| acc agc acc acc acc agc tcc ccg tcc ggt ccc acg ggc aac cct cct<br>Thr Ser Thr Thr Thr Ser Ser Pro Ser Gly Pro Thr Gly Asn Pro Pro<br>                    245                       250                     255 | 1664 |
| gga ggc ggt ggc tgc act gcc cag aag tgg gcc cag tgc ggc ggc act<br>Gly Gly Gly Gly Cys Thr Ala Gln Lys Trp Ala Gln Cys Gly Gly Thr<br>                    260                       265                     270 | 1712 |
| ggc ttc acg ggc tgc acc acc tgc gtc tcg ggc acc acc tgc cag gtg<br>Gly Phe Thr Gly Cys Thr Thr Cys Val Ser Gly Thr Thr Cys Gln Val<br>275                 280              285 | 1760 |
| cag aac cag tgg tat tcc cag tgt ctg tgagcgggag ggttgttggg<br>Gln Asn Gln Trp Tyr Ser Gln Cys Leu<br>290                 295 | 1807 |
| gtccgtttcc ctagggctga ggctgacgtg aactgggtcc tcttgtccgc cccatcacgg | 1867 |
| gttcgtattc gcgcgcttag ggagaggagg atgcagtttg agggggccac attttgaggg | 1927 |
| ggacgcagtc tggggtcgaa gcttgtcggt tagggctgcc gtgacgtggt agagcagatg | 1987 |

-continued

```
ggaccaagtg cggagctagg caggtgggtg gttgtggtgg tggcttacct tctgtaacgc    2047
aatggcatct catctcactc gcctgctccc tgattggtgg ctctgttcgg cctggcgctt    2107
tttgggaccg ctggctggaa tggattgctc cggaacgcca ggttgagctg ggctggcgcg    2167
agtagattgg ccgctccgag ctgcaaccat aataaaattt tcggaccctg taagccgcac    2227
ccgaccaggt ctccattggc ggacatgcac gacgtccttc gcaggcacgg cctgcccgcc    2287
tctgatcacc cgcagttttc gtaccgtcag accagataca agccccg                  2334
```

<210> SEQ ID NO 2
<211> LENGTH: 297
<212> TYPE: PRT
<213> ORGANISM: Acremonium thermophilum

<400> SEQUENCE: 2

```
Met Arg Ser Ser Pro Phe Leu Arg Ala Ala Leu Ala Ala Ala Leu Pro
 1               5                  10                  15

Leu Ser Ala His Ala Leu Asp Gly Lys Ser Thr Arg Tyr Trp Asp Cys
            20                  25                  30

Cys Lys Pro Ser Cys Gly Trp Pro Gly Lys Ala Ser Val Asn Gln Pro
        35                  40                  45

Val Phe Ser Cys Ser Ala Asp Trp Gln Arg Ile Ser Asp Phe Asn Ala
    50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
    130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
    210                 215                 220

Ala Ser Tyr Pro Val Phe Asn Pro Pro Ser Gly Gly Ser Pro Ser Thr
225                 230                 235                 240

Thr Ser Thr Thr Thr Ser Ser Pro Ser Gly Pro Thr Gly Asn Pro Pro
                245                 250                 255

Gly Gly Gly Gly Cys Thr Ala Gln Lys Trp Ala Gln Cys Gly Gly Thr
            260                 265                 270

Gly Phe Thr Gly Cys Thr Thr Cys Val Ser Gly Thr Thr Cys Gln Val
        275                 280                 285

Gln Asn Gln Trp Tyr Ser Gln Cys Leu
    290                 295
```

<210> SEQ ID NO 3

```
<211> LENGTH: 2033
<212> TYPE: DNA
<213> ORGANISM: Acremonium thermophilum
<220> FEATURE:
<221> NAME/KEY: CDS
<222> LOCATION: (259)...(702)
<220> FEATURE:
<221> NAME/KEY: intron
<222> LOCATION: (703)...(857)
<220> FEATURE:
<221> NAME/KEY: CDS
<222> LOCATION: (858)...(888)
<220> FEATURE:
<221> NAME/KEY: intron
<222> LOCATION: (889)...(990)
<220> FEATURE:
<221> NAME/KEY: CDS
<222> LOCATION: (991)...(1268)

<400> SEQUENCE: 3
```

| | |
|---|---:|
| ctcgaggaga ggaaccgagt ttgaaagatg ctatatatcg atagactacc ggcgtcgcct | 60 |
| cgccctgtcc gctctcttgc attcccctg ttgatgagac gagacaaaat tcctggttag | 120 |
| aaaagatccg tcgccgagat ttcaccagtg gtaagtcccg agaattggtc attcgacgtt | 180 |
| caatatgagt gtcaaagcta tgggtcctaa caaagaagga agcaagagct ttaaagagac | 240 |

| | | |
|---|---|---:|
| agaataacag cagcaaag atg cgt ctc cca cta ccg act ctg ctc gcc ctc | | 291 |
| Met Arg Leu Pro Leu Pro Thr Leu Leu Ala Leu | | |
| 1 5 10 | | |
| ttg ccc tac tac ctc gaa gtg tcc gct cag ggg gca tcc gga acc ggc | | 339 |
| Leu Pro Tyr Tyr Leu Glu Val Ser Ala Gln Gly Ala Ser Gly Thr Gly | | |
| 15 20 25 | | |
| acg aca aca cgt tac tgg gat tgc tgc aag ccg agc tgc gcg tgg cct | | 387 |
| Thr Thr Thr Arg Tyr Trp Asp Cys Cys Lys Pro Ser Cys Ala Trp Pro | | |
| 30 35 40 | | |
| ctg aag ggc aat tcg ccc agc ccg gtg cag act tgc gac aag aat gac | | 435 |
| Leu Lys Gly Asn Ser Pro Ser Pro Val Gln Thr Cys Asp Lys Asn Asp | | |
| 45 50 55 | | |
| agg ccg ctg aac gat ggg gga aac acc aag tcc ggc tgc gac aac ggt | | 483 |
| Arg Pro Leu Asn Asp Gly Gly Asn Thr Lys Ser Gly Cys Asp Asn Gly | | |
| 60 65 70 75 | | |
| ggc ggg gcc ttc atg tgc tca tcc cag agt ccc tgg gcc gtc aat gag | | 531 |
| Gly Gly Ala Phe Met Cys Ser Ser Gln Ser Pro Trp Ala Val Asn Glu | | |
| 80 85 90 | | |
| acc acc agc tac ggc tgg gca gcc gtt cgt atc gcc ggc agt acc gag | | 579 |
| Thr Thr Ser Tyr Gly Trp Ala Ala Val Arg Ile Ala Gly Ser Thr Glu | | |
| 95 100 105 | | |
| tcg gcc tgg tgc tgt gcc tgc tac gag ctc acc ttc acc agt ggg ccc | | 627 |
| Ser Ala Trp Cys Cys Ala Cys Tyr Glu Leu Thr Phe Thr Ser Gly Pro | | |
| 110 115 120 | | |
| gtc agt gga aag aag ctc ata gtc cag gcc acg aac act ggt gga gac | | 675 |
| Val Ser Gly Lys Lys Leu Ile Val Gln Ala Thr Asn Thr Gly Gly Asp | | |
| 125 130 135 | | |
| ctt ggg agc aac cac ttt gac ctt gcg gtatgtgggg tttttctttc | | 722 |
| Leu Gly Ser Asn His Phe Asp Leu Ala | | |
| 140 145 | | |
| ttcatcatcg ctctcaccat ggattcctcg gcgcaaggac caagattgag aagcgtcaat | | 782 |
| gccgggttgg acacgggagc cgggatagga acacagaggc cgtttaagac cgtcagctga | | 842 |
| cagcagagca attag att ccc gga ggt ggt gtt ggt cag tcc aat g | | 888 |
| Ile Pro Gly Gly Gly Val Gly Gln Ser Asn | | |
| 150 155 | | |
| gtaggttcct tccctgaagt accggcaaca gcctgtgcgt tgctgtatac ccctttaat | | 948 |

-continued

```
catagcatct tcctgctgga tacaagccaa cccattttct a gct tgc acg aac cag      1004
                                              Ala Cys Thr Asn Gln
                                                              160 tat ggt gcg ccc ccg aac ggc tgg ggc gac agg tat ggt ggc gtg cac        1052
Tyr Gly Ala Pro Pro Asn Gly Trp Gly Asp Arg Tyr Gly Gly Val His
    165                 170                 175 tcg cgg agc gac tgc gac agc ttc ccc gcg gcg ctc aag gcc ggc tgc        1100
Ser Arg Ser Asp Cys Asp Ser Phe Pro Ala Ala Leu Lys Ala Gly Cys
180                 185                 190                 195 tac tgg cga ttc gac tgg ttc cag ggc gcc gac aac ccg tcc gtg agc        1148
Tyr Trp Arg Phe Asp Trp Phe Gln Gly Ala Asp Asn Pro Ser Val Ser
                200                 205                 210 ttc aaa cag gta gcc tgc ccg gca gcc atc aca gct aag agc ggc tgt        1196
Phe Lys Gln Val Ala Cys Pro Ala Ala Ile Thr Ala Lys Ser Gly Cys
            215                 220                 225 act cgc cag aac gat gcc atc aac gag act ccg act ggg ccc agc act        1244
Thr Arg Gln Asn Asp Ala Ile Asn Glu Thr Pro Thr Gly Pro Ser Thr
        230                 235                 240 gtg cct acc tac acc gcg tca ggc tgaaagtcgg ctggggcacc attgcccagg       1298
Val Pro Thr Tyr Thr Ala Ser Gly
    245                 250 tgatggttgg gcatgtgtta gtctcactca ccagggacat ttgtcgcgac ctgatcatag      1358
gcgccagggg agttgaaagg ggttgccgta cgagaagaca ttttgtcgcc gtcttactcc      1418
cagccacttc tgtacatatt caatgacatt acatagcccg caaatatgtt catatatcgt     1478
ggccgcccaa accgcccggg tttgcttagg ctggagctga agtggctcgc cgatggctgt     1538
caaaggcagt cggaatattc ctcgttgctt cggcaacacg gtagctgctt gaaccgtacc     1598
cagcattaga acacccccg ccgagggctt gctacgtcaa tggcggggtc tccaaccct      1658
gcgcggcaca aaaccaacca cgccctcgtc ttttatgatg tcctcgctca aacgtcccgt     1718
gacgacactc cgctcatggt ctggtcctct gatgtagaag gggtaggtca gccgatggtc     1778
gtcaccgtcg tcaatgcttc cctcaagctt cttgcggcct ttatcctcca actcttccca     1838
catgagaact ccatctttcc gccttttcac aaagccactg ccctccttgt caagggccaa     1898
aaaccaacgc cgctgatgaa tgcttccgat cgtgtttgac gcgcccgggg tatgcatttg     1958
gttcggcgca ctttttttcgt cctccagctc ccttaactcc cgttccatct gagagggtga    2018
ctcgtctact cgact                                                      2033
```

<210> SEQ ID NO 4
<211> LENGTH: 251
<212> TYPE: PRT
<213> ORGANISM: Acremonium thermophilum

<400> SEQUENCE: 4

```
Met Arg Leu Pro Leu Pro Thr Leu Leu Ala Leu Leu Pro Tyr Tyr Leu
1               5                   10                  15

Glu Val Ser Ala Gln Gly Ala Ser Gly Thr Gly Thr Thr Thr Arg Tyr
                20                  25                  30

Trp Asp Cys Cys Lys Pro Ser Cys Ala Trp Pro Leu Lys Gly Asn Ser
            35                  40                  45

Pro Ser Pro Val Gln Thr Cys Asp Lys Asn Asp Arg Pro Leu Asn Asp
        50                  55                  60

Gly Gly Asn Thr Lys Ser Gly Cys Asp Asn Gly Gly Ala Phe Met
65                  70                  75                  80

Cys Ser Ser Gln Ser Pro Trp Ala Val Asn Glu Thr Thr Ser Tyr Gly
                85                  90                  95
```

```
Trp Ala Ala Val Arg Ile Ala Gly Ser Thr Glu Ser Ala Trp Cys Cys
                100                 105                 110
Ala Cys Tyr Glu Leu Thr Phe Thr Ser Gly Pro Val Ser Gly Lys Lys
            115                 120                 125
Leu Ile Val Gln Ala Thr Asn Thr Gly Gly Asp Leu Gly Ser Asn His
    130                 135                 140
Phe Asp Leu Ala Ile Pro Gly Gly Val Gly Gln Ser Asn Ala Cys
145                 150                 155                 160
Thr Asn Gln Tyr Gly Ala Pro Pro Asn Gly Trp Gly Asp Arg Tyr Gly
                165                 170                 175
Gly Val His Ser Arg Ser Asp Cys Asp Ser Phe Pro Ala Ala Leu Lys
            180                 185                 190
Ala Gly Cys Tyr Trp Arg Phe Asp Trp Phe Gln Gly Ala Asp Asn Pro
            195                 200                 205
Ser Val Ser Phe Lys Gln Val Ala Cys Pro Ala Ala Ile Thr Ala Lys
    210                 215                 220
Ser Gly Cys Thr Arg Gln Asn Asp Ala Ile Asn Glu Thr Pro Thr Gly
225                 230                 235                 240
Pro Ser Thr Val Pro Thr Tyr Thr Ala Ser Gly
                245                 250

<210> SEQ ID NO 5
<211> LENGTH: 17
<212> TYPE: PRT
<213> ORGANISM: Acremonium thermophilum

<400> SEQUENCE: 5

Gln Ser Cys Ser Ser Phe Pro Ala Pro Leu Lys Pro Gly Cys Gln Trp
1               5                   10                  15
Arg

<210> SEQ ID NO 6
<211> LENGTH: 13
<212> TYPE: PRT
<213> ORGANISM: Acremonium thermophilum

<400> SEQUENCE: 6

Tyr Ala Leu Thr Phe Asn Ser Gly Pro Val Ala Gly Lys
1               5                   10

<210> SEQ ID NO 7
<211> LENGTH: 10
<212> TYPE: PRT
<213> ORGANISM: Acremonium thermophilum

<400> SEQUENCE: 7

Val Gln Cys Pro Ser Glu Leu Thr Ser Arg
1               5                   10

<210> SEQ ID NO 8
<211> LENGTH: 13
<212> TYPE: PRT
<213> ORGANISM: Acremonium thermophilum

<400> SEQUENCE: 8

Asn Gln Pro Val Phe Ser Cys Ser Ala Asp Trp Gln Arg
1               5                   10

<210> SEQ ID NO 9
```

-continued

```
<211> LENGTH: 14
<212> TYPE: PRT
<213> ORGANISM: Acremonium thermophilum

<400> SEQUENCE: 9

Tyr Trp Asp Cys Cys Lys Pro Ser Cys Gly Trp Pro Gly Lys
 1               5                  10

<210> SEQ ID NO 10
<211> LENGTH: 4
<212> TYPE: PRT
<213> ORGANISM: Acremonium thermophilum

<400> SEQUENCE: 10

Pro Thr Phe Thr
 1

<210> SEQ ID NO 11
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3
<223> OTHER INFORMATION: y = C or T
<220> FEATURE:
<221> NAME/KEY: misc_feature
<222> LOCATION: 9
<223> OTHER INFORMATION: y = C or T
<220> FEATURE:
<221> NAME/KEY: misc_feature
<222> LOCATION: 12
<223> OTHER INFORMATION: y = C or T
<220> FEATURE:
<221> NAME/KEY: misc_feature
<222> LOCATION: 15
<223> OTHER INFORMATION: y = C or T
<220> FEATURE:
<221> NAME/KEY: misc_feature
<222> LOCATION: 18
<223> OTHER INFORMATION: r = A or G

<400> SEQUENCE: 11
taytgggayt gytgyaarcc                                                 20

<210> SEQ ID NO 12
<211> LENGTH: 21
<212> TYPE: DNA
<213> ORGANISM: Artificial Sequence
<220> FEATURE:
<221> NAME/KEY: misc_feature
<222> LOCATION: 1
<223> OTHER INFORMATION: r = A or G
<220> FEATURE:
<221> NAME/KEY: misc_feature
<222> LOCATION: 4
<223> OTHER INFORMATION: r = A or G
<220> FEATURE:
<221> NAME/KEY: misc_feature
<222> LOCATION: 7
<223> OTHER INFORMATION: n = A,T,C or G
<220> FEATURE:
<221> NAME/KEY: misc_feature
<222> LOCATION: 10
<223> OTHER INFORMATION: r = A or G
<220> FEATURE:
<221> NAME/KEY: misc_feature
<222> LOCATION: 13
<223> OTHER INFORMATION: y = C or T
<220> FEATURE:
<221> NAME/KEY: misc_feature
```

```
<222> LOCATION: 16
<223> OTHER INFORMATION: r = A or G
<220> FEATURE:
<223> OTHER INFORMATION: primer

<400> SEQUENCE: 12
rttrtcngcr ttytgraacc a                                              21

<210> SEQ ID NO 13
<211> LENGTH: 7
<212> TYPE: PRT
<213> ORGANISM: Melanocarpus albomyces

<400> SEQUENCE: 13

Trp Phe Gln Asn Ala Asp Asn
 1               5

<210> SEQ ID NO 14
<211> LENGTH: 636
<212> TYPE: DNA
<213> ORGANISM: Acremonium thermophilum

<400> SEQUENCE: 14
tactgggatt gttgcaagcc gtcctgcggc tggccgggaa aggcctcggt gaaccagccc      60
gtcttctcgt gctcggccga ctggcagcgc atcagcgact tcaacgcgaa gtcgggctgc     120
gacggaggct ccgcctactc gtgcgccgac cagacgccct gggcggtcaa cgacaacttc     180
tcgtacggct cgcagccac ggccatcgcc ggcggctccg agtccagctg gtgctgcgcc      240
tgctatgcgt gagttctctg caagccgctt cccaccccg ctttctgtgc aggccgcttc      300 cccctaccc acccacttcc ccccccgc tctgtgatc gggcatccga gctaagttgc         360
gtgtcgtcca gactcacctt caactcgggc cccgtcgcgg caagaccat ggtggtgcag      420 tcgaccagca ccggcggcga cctgggcagc aaccagttcg acctcgccat ccccggcggc     480
ggcgtgggca tcttcaacgg ctgcgcctcc cagttcggcg gcctccccgg cgcccagtac     540
ggcggcatca cgaccgcag ccagtgctcg tccttccccg cgccgctcca gccgggctgc     600
cagtggcgct cgactggtt ccagaacgcg gataat                               636

<210> SEQ ID NO 15
<211> LENGTH: 786
<212> TYPE: DNA
<213> ORGANISM: Acremonium thermophilum

<400> SEQUENCE: 15
tactgggatt gttgcaagcc gagctgcgcg tggcctctga agggcaattc gcccagcccg      60
gtgcagactt gcgacaagaa tgacaggccg ctgaacgatg ggggaaacac caagtccggc    120
tgcgacaacg gtggcggggc cttcatgtgc tcatcccaga gtccctgggc cgtcaatgag    180
accaccagct acggctgggc agccgttcgt atcgccggca gtaccgagtc ggcctggtgc    240
tgtgcctgct acgagctcac cttcaccagt gggcccgtca gtggaaagaa gctcatagtc    300
caggccacga acactggtgg agaccttggg agcaaccact tgaccttgc ggtatgtggg     360 gttttttctt cttcatcatc gctctcacca tggattcctc ggcgcaagga ccaagattga    420
gaagcgtcaa tgccgggttg gacacgggag ccgggatagg aacacagagg ccgtttaaga    480
ccgtcagctg acagcaggag caattagatt cccggaggtg gtgttggtca gttcaatggt    540
aggttccttc cctgaagtac cggcaacagc ctgtgcgttg ctgtataccc cttttaatca    600
tagcatcttc ctgctggata caagccaacc cattttctag cttgcacgaa ccagtatggt    660
```

-continued

```
gcgcccccga acggctgggg cgacaggtat ggtggcgtgc actcgcggag cgactgcgac    720
agcttccccg cggcgctcaa ggccggctgc tactggcgat tcgactggtt tcaaaacgcc    780
gacaac                                                                786

<210> SEQ ID NO 16
<211> LENGTH: 994
<212> TYPE: DNA
<213> ORGANISM: Acremonium thermophilum
<220> FEATURE:
<221> NAME/KEY: CDS
<222> LOCATION: (13)...(95)
<220> FEATURE:
<221> NAME/KEY: intron
<222> LOCATION: (96)...(154)
<220> FEATURE:
<221> NAME/KEY: CDS
<222> LOCATION: (155)...(403)
<220> FEATURE:
<221> NAME/KEY: intron
<222> LOCATION: (404)...(526)
<220> FEATURE:
<221> NAME/KEY: CDS
<222> LOCATION: (527)...(986)

<400> SEQUENCE: 16
ggactgcgca tc atg cgc tcc tca ccc ttt ctc cgc gca gct ctg gct gcc    51
              Met Arg Ser Ser Pro Phe Leu Arg Ala Ala Leu Ala Ala
              1               5                   10 gct ctg cct ctg agc gcc cat gcc ctc gac gga aag tcg acg ag           95
Ala Leu Pro Leu Ser Ala His Ala Leu Asp Gly Lys Ser Thr Thr
        15                  20                  25 gtatgccaat cctcgtacct ctgccctctg tagaaacaag tgaccgactg caaagacag    154 ata ctg gga ctg ctg caa gcc gtc ctg cgg ctg ggc cgg aaa ggc ctc     202
Ile Leu Gly Leu Leu Gln Ala Val Leu Arg Leu Gly Arg Lys Gly Leu
    30                  35                  40 ggt gaa cca gcc cgt ctt ctc gtg ctc ggc cga ctg gca gcg cat cag     250
Gly Glu Pro Ala Arg Leu Leu Val Leu Gly Arg Leu Ala Ala His Gln
45                  50                  55                  60 cga ctt caa cgc gaa gtc ggg ctg cga cgg agg ctc cgc cta ctc gtg     298
Arg Leu Gln Arg Glu Val Gly Leu Arg Arg Arg Leu Arg Leu Leu Val
                65                  70                  75 cgc cga cca gac gcc ctg ggc ggt caa cga caa ctt ctc gta cgg ctt     346
Arg Arg Pro Asp Ala Leu Gly Gly Gln Arg Gln Leu Leu Val Arg Leu
            80                  85                  90 cgc agc cac ggc cat cgc cgg cgg ctc cga gtc cag ctg gtg ctg cgc     394
Arg Ser His Gly His Arg Arg Arg Leu Arg Val Gln Leu Val Leu Arg
        95                  100                 105 ctg cta tgc gtgagttctc tgcaagccgc ttcccacccc cgctttctgt             443
Leu Leu Cys
    110 gcaggccgct tcccccctac ccacccactt cccccccccc gcctctgtga tcgggcatcc   503 gagctaagtt gcgtgtcgtc cag act cac ctt caa ctc ggg ccc cgt cgc ggg   556
                         Thr His Leu Gln Leu Gly Pro Arg Arg Gly
                                     115                 120 caa gac cat ggt ggt gca gtc gac cag cac cgg cgg cga cct ggg cag     604
Gln Asp His Gly Gly Ala Val Asp Gln His Arg Arg Arg Pro Gly Gln
            125                 130                 135 caa cca gtt cga cct cgc cat ccc cgg cgg cgg cgt ggg cat ctt caa     652
Gln Pro Val Arg Pro Arg His Pro Arg Arg Arg Arg Gly His Leu Gln
        140                 145                 150 cgg ctg cgc ctc cca gtt cgg cgg cct ccc cgg cgc cca gta cgg cgg     700
```

-continued

```
Arg Leu Arg Leu Pro Val Arg Arg Pro Pro Arg Arg Pro Val Arg Arg
    155                 160                 165 cat cag cga ccg cag cca gtg ctc gtc ctt ccc cgc gcc gct cca gcc     748
His Gln Arg Pro Gln Pro Val Leu Val Leu Pro Arg Ala Ala Pro Ala
170                 175                 180                 185 ggg ctg cca gtg gcg ctt cga ctg gtt cca gaa cgc cga caa ccc cac     796
Gly Leu Pro Val Ala Leu Arg Leu Val Pro Glu Arg Arg Gln Pro His
                190                 195                 200 ctt cac ctt cca gcg cgt gca gtg ccc gtc cga gct cac gtc ccg cac     844
Leu His Leu Pro Ala Arg Ala Val Pro Val Arg Ala His Val Pro His
            205                 210                 215 ggg ctg taa gcg cga cga cga cgc cag cta tcc cgt ctt caa ccc gcc     892
Gly Leu  *  Ala Arg Arg Arg Arg Gln Leu Ser Arg Leu Gln Pro Ala
        220                 225                 230 tag cgg tgg ctc ccc cag cac cac cag cac cac cac cag ctc ccc gtc     940
 *  Arg Trp Leu Pro Gln His His Gln His His His Gln Leu Pro Val
            235                 240                 245 cgg tcc cac ggg caa ccc tcc tgg agg cgg tgg ctg cac tgc cca g       986
Arg Ser His Gly Gln Pro Ser Trp Arg Arg Trp Leu His Cys Pro
        250                 255                 260 tgactgca                                                            994

<210> SEQ ID NO 17
<211> LENGTH: 264
<212> TYPE: PRT
<213> ORGANISM: Acremonium thermophilum

<400> SEQUENCE: 17

Met Arg Ser Ser Pro Phe Leu Arg Ala Ala Leu Ala Ala Ala Leu Pro
 1               5                  10                  15

Leu Ser Ala His Ala Leu Asp Gly Lys Ser Thr Arg Tyr Trp Asp Cys
                20                  25                  30

Cys Lys Pro Ser Cys Gly Trp Ala Gly Lys Ala Ser Val Asn Gln Pro
            35                  40                  45

Val Phe Ser Cys Ser Ala Asp Trp Gln Arg Ile Ser Asp Phe Asn Ala
        50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
    210                 215                 220
```

```
Ala Ser Tyr Pro Val Phe Asn Pro Pro Ser Gly Gly Ser Pro Ser Thr
225                 230                 235                 240

Thr Ser Thr Thr Thr Ser Ser Pro Ser Gly Pro Thr Gly Asn Pro Pro
            245                 250                 255

Gly Gly Gly Gly Cys Thr Ala Gln
            260

<210> SEQ ID NO 18
<211> LENGTH: 907
<212> TYPE: DNA
<213> ORGANISM: Acremonium thermophilum
<220> FEATURE:
<221> NAME/KEY: CDS
<222> LOCATION: (13)...(95)
<220> FEATURE:
<221> NAME/KEY: intron
<222> LOCATION: (96)...(154)
<220> FEATURE:
<221> NAME/KEY: CDS
<222> LOCATION: (155)...(403)
<220> FEATURE:
<221> NAME/KEY: intron
<222> LOCATION: (404)...(526)
<220> FEATURE:
<221> NAME/KEY: CDS
<222> LOCATION: (527)...(899)

<400> SEQUENCE: 18
ggactgcgca tc atg cgc tcc tca ccc ttt ctc cgc gca gct ctg gct gcc         51
              Met Arg Ser Ser Pro Phe Leu Arg Ala Ala Leu Ala Ala
              1               5                   10 gct ctg cct ctg agc gcc cat gcc ctc gac gga aag tcg acg ag                95
Ala Leu Pro Leu Ser Ala His Ala Leu Asp Gly Lys Ser Thr Arg
    15                  20                  25 gtatgccaat cctcgtacct ctgccctctg tagaaacaag tgaccgactg caaagacag         154 a tac tgg gac tgc tgc aag ccg tcc tgc ggc tgg gcc gga aag gcc tcg        203
  Tyr Trp Asp Cys Cys Lys Pro Ser Cys Gly Trp Ala Gly Lys Ala Ser
      30                  35                  40 gtg aac cag ccc gtc ttc tcg tgc tcg gcc gac tgg cag cgc atc agc         251
Val Asn Gln Pro Val Phe Ser Cys Ser Ala Asp Trp Gln Arg Ile Ser
45                  50                  55                  60 gac ttc aac gcg aag tcg ggc tgc gac gga ggc tcc gcc tac tcg tgc         299
Asp Phe Asn Ala Lys Ser Gly Cys Asp Gly Gly Ser Ala Tyr Ser Cys
            65                  70                  75 gcc gac cag acg ccc tgg gcg gtc aac gac aac ttc tcg tac ggc ttc         347
Ala Asp Gln Thr Pro Trp Ala Val Asn Asp Asn Phe Ser Tyr Gly Phe
                80                  85                  90 gca gcc acg gcc atc gcc ggc ggc tcc gag tcc agc tgg tgc tgc gcc         395
Ala Ala Thr Ala Ile Ala Gly Gly Ser Glu Ser Ser Trp Cys Cys Ala
            95                  100                 105 tgc tat gc gtgagttctc tgcaagccgc ttcccacccc cgctttctgt                    443
Cys Tyr Ala
        110 gcaggccgct tcccccctac ccacccactt ccccccccc gcctctgtga tcgggcatcc          503 gagctaagtt gcgtgtcgtc cag a ctc acc ttc aac tcg ggc ccc gtc gcg          554
                           Leu Thr Phe Asn Ser Gly Pro Val Ala
                                    115                 120 ggc aag acc atg gtg gtg cag tcg acc agc acc ggc ggc gac ctg ggc          602
Gly Lys Thr Met Val Val Gln Ser Thr Ser Thr Gly Gly Asp Leu Gly
                125                 130                 135 agc aac cag ttc gac ctc gcc atc ccc ggc ggc ggc gtg ggc atc ttc          650
Ser Asn Gln Phe Asp Leu Ala Ile Pro Gly Gly Gly Val Gly Ile Phe
            140                 145                 150
```

```
aac ggc tgc gcc tcc cag ttc ggc ggc ctc ccc ggc gcc cag tac ggc      698
Asn Gly Cys Ala Ser Gln Phe Gly Gly Leu Pro Gly Ala Gln Tyr Gly
            155                 160                 165 ggc atc agc gac cgc agc cag tgc tcg tcc ttc ccc gcg ccg ctc cag      746
Gly Ile Ser Asp Arg Ser Gln Cys Ser Ser Phe Pro Ala Pro Leu Gln
170                 175                 180 ccg ggc tgc cag tgg cgc ttc gac tgg ttc cag aac gcc gac aac ccc      794
Pro Gly Cys Gln Trp Arg Phe Asp Trp Phe Gln Asn Ala Asp Asn Pro
185                 190                 195                 200 acc ttc acc ttc cag cgc gtg cag tgc ccg tcc gag ctc acg tcc cgc      842
Thr Phe Thr Phe Gln Arg Val Gln Cys Pro Ser Glu Leu Thr Ser Arg
                205                 210                 215 acg ggc tgt aag cgc gac gac gac gcc agc tat ccc gtc ttc aac ccg      890
Thr Gly Cys Lys Arg Asp Asp Asp Ala Ser Tyr Pro Val Phe Asn Pro
            220                 225                 230 cct agc ggt tgactgca                                                 907
Pro Ser Gly
        235

<210> SEQ ID NO 19
<211> LENGTH: 235
<212> TYPE: PRT
<213> ORGANISM: Acremonium thermophilum

<400> SEQUENCE: 19

Met Arg Ser Ser Pro Phe Leu Arg Ala Ala Leu Ala Ala Ala Leu Pro
1               5                   10                  15

Leu Ser Ala His Ala Leu Asp Gly Lys Ser Thr Arg Tyr Trp Asp Cys
                20                  25                  30

Cys Lys Pro Ser Cys Gly Trp Ala Gly Lys Ala Ser Val Asn Gln Pro
            35                  40                  45

Val Phe Ser Cys Ser Ala Asp Trp Gln Arg Ile Ser Asp Phe Asn Ala
        50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
210                 215                 220

Ala Ser Tyr Pro Val Phe Asn Pro Pro Ser Gly
225                 230                 235
```

```
<210> SEQ ID NO 20
<211> LENGTH: 1175
<212> TYPE: DNA
<213> ORGANISM: Acremonium thermophilum
<220> FEATURE:
<221> NAME/KEY: CDS
<222> LOCATION: (1)...(444)
<220> FEATURE:
<221> NAME/KEY: intron
<222> LOCATION: (445)...(599)
<220> FEATURE:
<221> NAME/KEY: CDS
<222> LOCATION: (600)...(630)
<220> FEATURE:
<221> NAME/KEY: intron
<222> LOCATION: (631)...(732)
<220> FEATURE:
<221> NAME/KEY: CDS
<222> LOCATION: (733)...(1172)

<400> SEQUENCE: 20 atg cgt ctc cca cta ccg act ctg ctc gcc ctc ttg ccc tac tac ctc      48
Met Arg Leu Pro Leu Pro Thr Leu Leu Ala Leu Leu Pro Tyr Tyr Leu
1               5                   10                  15 gaa gtg tcc gct cag ggg gca tcc gga acc ggc acg aca aca cgt tac      96
Glu Val Ser Ala Gln Gly Ala Ser Gly Thr Gly Thr Thr Thr Arg Tyr
            20                  25                  30 tgg gat tgc tgc aag ccg agc tgc gcg tgg cct ctg aag ggc aat tcg     144
Trp Asp Cys Cys Lys Pro Ser Cys Ala Trp Pro Leu Lys Gly Asn Ser
        35                  40                  45 ccc agc ccg gtg cag act tgc gac aag aat gac agg ccg ctg aac gat     192
Pro Ser Pro Val Gln Thr Cys Asp Lys Asn Asp Arg Pro Leu Asn Asp
    50                  55                  60 ggg gga aac acc aag tcc ggc tgc gac aac ggt ggc ggg gcc ttc atg     240
Gly Gly Asn Thr Lys Ser Gly Cys Asp Asn Gly Gly Gly Ala Phe Met
65                  70                  75                  80 tgc tca tcc cag agt ccc tgg gcc gtc aat gag acc acc agc tac ggc     288
Cys Ser Ser Gln Ser Pro Trp Ala Val Asn Glu Thr Thr Ser Tyr Gly
                85                  90                  95 tgg gca gcc gtt cgt atc gcc ggc agt acc gag tcg gcc tgg tgc tgt     336
Trp Ala Ala Val Arg Ile Ala Gly Ser Thr Glu Ser Ala Trp Cys Cys
            100                 105                 110 gcc tgc tac gag ctc acc ttc acc agt ggg ccc gtc agt gga aag aag     384
Ala Cys Tyr Glu Leu Thr Phe Thr Ser Gly Pro Val Ser Gly Lys Lys
        115                 120                 125 ctc ata gtc cag gcc acg aac act ggt gga gac ctt ggg agc aac cac     432
Leu Ile Val Gln Ala Thr Asn Thr Gly Gly Asp Leu Gly Ser Asn His
    130                 135                 140 ttt gac ctt gcg gtatgtgggg tttttctttc ttcatcatcg ctctcaccat         484
Phe Asp Leu Ala
145 ggattcctcg gcgcaaggac caagattgag aagcgtcaat gccgggttgg acacgggagc   544 cgggatagga acacagaggc cgtttaagac cgtcagctga cagcagagca attag att    602
                                                              Ile ccc gga ggt ggt gtt ggt cag tcc aat g gtaggttcct tccctgaagt         650
Pro Gly Gly Gly Val Gly Gln Ser Asn
150                 155 accggcaaca gcctgtgcgt tgctgtatac ccctttttaat catagcatct tcctgctgga  710
tacaagccaa cccatttttct a   gct tgc acg aac cag tat ggt gcg ccc ccg   761
                         Ala Cys Thr Asn Gln Tyr Gly Ala Pro Pro
                                 160                 165 aac ggc tgg ggc gac agg tat ggt ggc gtg cac tcg cgg agc gac tgc     809
Asn Gly Trp Gly Asp Arg Tyr Gly Gly Val His Ser Arg Ser Asp Cys
```

```
        170                 175                 180
gac agc ttc ccc gcg gcg ctc aag gcc ggc tgc tac tgg cga ttc gac      857
Asp Ser Phe Pro Ala Ala Leu Lys Ala Gly Cys Tyr Trp Arg Phe Asp
185                 190                 195                 200 tgg ttc cag ggc gcc gac aac ccg tcc gtg agc ttc aaa cag gta gcc      905
Trp Phe Gln Gly Ala Asp Asn Pro Ser Val Ser Phe Lys Gln Val Ala
                205                 210                 215 tgc ccg gca gcc atc aca gct aag agc ggc tgt act cgc cag aac gat      953
Cys Pro Ala Ala Ile Thr Ala Lys Ser Gly Cys Thr Arg Gln Asn Asp
                220                 225                 230 gcc atc aac gag act ccg act ggg ccc agc ggt ggc tcc ccc agc acc     1001
Ala Ile Asn Glu Thr Pro Thr Gly Pro Ser Gly Gly Ser Pro Ser Thr
                235                 240                 245 acc agc acc acc acc agc tcc ccg tcc ggt ccc acg ggc aac cct cct     1049
Thr Ser Thr Thr Thr Ser Ser Pro Ser Gly Pro Thr Gly Asn Pro Pro
250                 255                 260 gga ggc ggt ggc tgc act gcc cag aag tgg gcc cag tgc ggc ggc act     1097
Gly Gly Gly Gly Cys Thr Ala Gln Lys Trp Ala Gln Cys Gly Gly Thr
265                 270                 275                 280 ggc ttc acg ggc tgc acc acc tgc gtc tcg ggc acc acc tgc cag gtg     1145
Gly Phe Thr Gly Cys Thr Thr Cys Val Ser Gly Thr Thr Cys Gln Val
                285                 290                 295 cag aac cag tgg tat tcc cag tgt ctg tga                             1175
Gln Asn Gln Trp Tyr Ser Gln Cys Leu
                300                 305

<210> SEQ ID NO 21
<211> LENGTH: 305
<212> TYPE: PRT
<213> ORGANISM: Acremonium thermophilum

<400> SEQUENCE: 21

Met Arg Leu Pro Leu Pro Thr Leu Leu Ala Leu Leu Pro Tyr Tyr Leu
1               5                   10                  15

Glu Val Ser Ala Gln Gly Ala Ser Gly Thr Gly Thr Thr Thr Arg Tyr
                20                  25                  30

Trp Asp Cys Cys Lys Pro Ser Cys Ala Trp Pro Leu Lys Gly Asn Ser
            35                  40                  45

Pro Ser Pro Val Gln Thr Cys Asp Lys Asn Asp Arg Pro Leu Asn Asp
        50                  55                  60

Gly Gly Asn Thr Lys Ser Gly Cys Asp Asn Gly Gly Ala Phe Met
65                  70                  75                  80

Cys Ser Ser Gln Ser Pro Trp Ala Val Asn Glu Thr Thr Ser Tyr Gly
                85                  90                  95

Trp Ala Ala Val Arg Ile Ala Gly Ser Thr Glu Ser Ala Trp Cys Cys
                100                 105                 110

Ala Cys Tyr Glu Leu Thr Phe Thr Ser Gly Pro Val Ser Gly Lys Lys
            115                 120                 125

Leu Ile Val Gln Ala Thr Asn Thr Gly Gly Asp Leu Gly Ser Asn His
    130                 135                 140

Phe Asp Leu Ala Ile Pro Gly Gly Gly Val Gly Gln Ser Asn Ala Cys
145                 150                 155                 160

Thr Asn Gln Tyr Gly Ala Pro Pro Asn Gly Trp Gly Asp Arg Tyr Gly
                165                 170                 175

Gly Val His Ser Arg Ser Asp Cys Asp Ser Phe Pro Ala Ala Leu Lys
                180                 185                 190

Ala Gly Cys Tyr Trp Arg Phe Asp Trp Phe Gln Gly Ala Asp Asn Pro
```

```
                        195                 200                 205
Ser Val Ser Phe Lys Gln Val Ala Cys Pro Ala Ala Ile Thr Ala Lys
    210                 215                 220

Ser Gly Cys Thr Arg Gln Asn Asp Ala Ile Asn Glu Thr Pro Thr Gly
225                 230                 235                 240

Pro Ser Gly Gly Ser Pro Ser Thr Thr Ser Thr Thr Thr Ser Ser Pro
                245                 250                 255

Ser Gly Pro Thr Gly Asn Pro Pro Gly Gly Gly Cys Thr Ala Gln
            260                 265                 270

Lys Trp Ala Gln Cys Gly Gly Thr Gly Phe Thr Gly Cys Thr Thr Cys
        275                 280                 285

Val Ser Gly Thr Thr Cys Gln Val Gln Asn Gln Trp Tyr Ser Gln Cys
    290                 295                 300

Leu
305
```

ENZYMES

FIELD OF THE INVENTION

The present invention relates to novel cellulase enzymes, especially novel endoglucanases including endoglucanase fusion proteins, preparations and compositions containing these endoglucanase enzymes and fusion proteins, expression vectors, host cells and methods for their preparation and uses of the cellulases, preparations and compositions in the textile, detergent and pulp and paper industries.

BACKGROUND OF THE INVENTION

Cellulose is the major structural component of higher plants and occurs naturally in almost pure form only in cotton fiber. It provides plant cells with high tensile strength helping them to resist mechanical stress and osmotic pressure. Cellulose is a linear polysaccharide of glucose residues connected by β-1,4 linkages. In nature, cellulose is usually associated with lignin together with hemicelluloses, such as xylans and glucomannans. Cellulolytic enzymes hydrolyze cellulose and are produced by a wide variety of bacteria and fungi. Cellulases are industrially important enzymes with a current annual market value of about 190 million U.S. $. In the textile industry, cellulases are used in denim finishing to create a fashionable stone washed appearance in denim cloths in a biostoning process, and they are also used, for instance, to clean fuzz and prevent formation of pills on the surface of cotton garments. In detergent industry cellulases are used to brighten colors and to prevent graying and pilling of garments. Cellulases are further used in food industry and animal feed manufacturing, and they have a great potential in the pulp and paper industry, for instance, in deinking to release ink from fiber surfaces and in improving pulp drainage. The wide spectrum of industrial uses for cellulases has established a need for commercial cellulase products containing different cellulase components and functioning optimally in different pH and temperature ranges.

The practical use of cellulases is hampered by the nature of the known cellulase compositions, which are often enzyme mixtures having a variety of activities and substrate specificities. For this reason, efforts have been made to obtain cellulases having only the desired activities. The unique properties of each cellulase make some more suitable for certain purposes than others. While the enzymes differ in a number of ways, one of the most important differences is the pH optimum. Neutral cellulases are most active in the pH range 6–8 and alkaline cellulases in the pH range 7.5–10, whereas acid cellulases, having the pH optimum at pH 4.5–5.5, show very low activity levels at higher pH values. Neutral and acid cellulases are especially useful in the textile industry. In fabric treatment cellulases attack the chains of cellulose molecules that form the cotton fibers, thereby affecting the characteristics of the fabric.

In textile industry "stone washed" look or an abraded look has been denim producers' interest in recent years. Traditional stone washing with pumice stones reduces the strength of fabric and burdens the laundering apparatuses. The trend has been towards enzymatic denim finishing processes and cellulases have replaced or are being used together with pumice stones to give the fabric its desired "worn" look. Controlled enzyme treatments result in less damage to the garments and machines and eliminate the need for disposal of stones.

Additionally, textile industry uses cellulases in biofinishing, i.e. to create permanent improvement of depilling and improved pilling resistance, cleared surface structure by reduced fuzz, improved textile handle, such as softness, smoothness and a silkier feel, improved drapability and brighter colors of the textile and improved moisture absorbability.

Cellulases applied in denim treatment are usually divided into two main groups: acid and neutral cellulases. Acid cellulases typically operate at pH 4.0–5.5 and the neutral cellulases in the range of pH 6–8. Acid cellulases used in biostoning mainly originate from *Trichoderma reesei* (sexual form *Hypocrea jecorina*) and the neutral cellulases come from a variety of fungi, including genera of *Melanocarpus, Humicola, Myceliophthora, Fusarium, Acremonium*, and *Chrysosporium* (Haakana et al. 2004). *T. reesei* enzymes include, e.g., cellulases from the glycoside family 5 (endoglucanase II, EGII), family 7 (cellobiohydrolase I, CBHI) and family 12 (endoglucanase III, EGIII; Ward et al. 1993), and the neutral cellulases, most often endoglucanases, from family 45 and family 7 (Henrissat, 1991; Henrissat and Bairoch, 1993, 1996).

Cellulases comprise a catalytic domain/core (CD) expressing cellulase activity. In addition to the catalytic domain the cellulase molecule may comprise one or more cellulose binding domains (CBDs), also named as carbohydrate binding domains/modules (CBD/CBM), which can be located either at the N- or C-terminus of the catalytic domain. CBDs have carbohydrate-binding activity and they mediate the binding of the cellulase to crystalline cellulose but have little or no effect on cellulase hydrolytic activity of the enzyme on soluble substrates. These two domains are typically connected via a flexible and highly glycosylated linker region.

Cellulases that attack primarily on the surface of the fiber are especially useful in stone washing of denim dyed with Indigo dye, as the dye is located on the surface of the fiber. When used to treat cotton fabric, acid cellulases generally require a shorter washing time than neutral cellulases. Acid cellulases are especially used in biofinishing (depilling) and also in denim treatment (biostoning).

Endoglucanases (EGs) in connection of the present invention mean enzymes classified as E.C. 3.2.1.4 and are one of the three types of cellulases generally needed for the biological conversion of cellulose to glucose. Endoglucanases cut internal beta-1,4-glucosidic bonds, whereas cellobiohydrolases cut the disaccharide cellobiose from the end of the cellulose polymer chain and beta-1,4-glucosidases hydrolyze the cellobiose and other short cello-oligosaccharides to glucose. Some naturally occurring endoglucanases have a cellulose-binding domain (CBD), while others do not.

Also endoglucanases are widely used in textile, detergent, and pulp and paper industry. For instance, endoglucanases of the cel45 family (EGs fam 45) are described, e.g., in U.S. Pat. No. 6,001,639, which describes enzymes having endoglucanase activity and having two conserved amino acid sequences. Uses in textile, detergent, and pulp and paper applications are generally discussed and treating of lignocellulosic material is mentioned. WO 2004/053039 is directed to detergent applications of endoglucanases. U.S. Pat. No. 5,958,082 discloses the use of endoglucanase, especially from *Thielavia terrestris* in textile applications providing stoned washed or abraded look of twill jeans. EP 0495258 relates to detergent compositions containing *Humicola* cellulase. U.S. Pat. No. 5,948,672 describes a cellulase preparation containing endoglucanase, especially from *Humicola* and its use in textile and pulp applications.

EG:s and EG-enriched compositions and concentrates are also commercially available.

However, there is a continuous need for improved cellulases, including endoglucanases that are more efficient in fabric treatment and in other fields, where cellulases traditionally are used. In particular, there is a continuous need for more efficient cellulases to improve the process economics.

The present invention aims to meet this need.

BRIEF DESCRIPTION OF THE INVENTION

An object of the present invention is to provide novel endoglucanases and endoglucanase fusion proteins having improved hydrolytic properties for use in textile industry, especially in cotton finishing processes, such as in depilling, and stone washing denim, and for use in detergent compositions as well as in other fields. The novel endoglucanases and endoglucanase fusion proteins of the invention have the advantage of being active at acid and neutral pH values, they have highly improved performance in textile biofinishing and biostoning applications and in detergent applications. When used in treating cellulose-containing textile materials, the novel endoglucanases and endoglucanase fusion proteins provide a smooth feel, improved appearance and softness as well as permanent depilling to the textile. With the improved efficiency of the endoglucanases of the invention, the use of the enzymes is significantly more economical. Additional advantages are achieved also in terms of logistics and the storage of the enzyme products, when smaller amounts of the enzyme product are needed. Furthermore, the novel endoglucanases and endoglucanase fusion proteins of the present invention, as being acidic, act more rapidly, affording time- and cost-effective treatment procedures and savings in equipment as well as treatment facilities.

A further object of the present invention is to provide polynucleotides encoding the novel endoglucanases and endoglucanase fusion proteins of the present invention.

A still further object of the present invention is to provide novel expression plasmids or vectors containing such polynucleotides, useful for the production of the novel endoglucanases and endoglucanase fusion proteins of the present invention, as well as novel hosts transformed with said expression plasmids.

A still further object of the present invention is to provide enzyme preparations, which contain one or more novel endoglucanases and endoglucanase fusion proteins having improved hydrolytic properties.

A still further object of the present invention is to provide methods of using the enzyme preparations and the endoglucanases and endoglucanase fusion proteins for finishing of textiles, especially for biofinishing and biostoning of denim.

A still further object of the present invention is to provide means for the use of the enzyme preparations of the invention in detergent compositions.

The present invention relates to an endoglucanase polypeptide comprising a fragment having cellulolytic activity and being selected from the group consisting of:

a) a polypeptide comprising an amino acid sequence having at least 78% identity to SEQ ID NO: 2 or an amino acid sequence having at least 68% identity to SEQ ID NO: 4;

b) a variant of a) comprising a fragment having cellulolytic activity; and c) a fragment of a) or b) having cellulolytic activity.

The present invention also relates to an endoglucanase fusion protein comprising an amino acid sequence derived from a polypeptide comprising an amino acid sequence having at least 68% identity to SEQ ID NO: 4 attached to a cellulose binding domain.

The present invention further relates to an isolated polynucleotide encoding the above defined endoglucanase polypeptide, selected from the group consisting of:

a) a nucleotide sequence of SEQ ID NO: 1, SEQ ID NO: 3, SEQ ID NO: 16, SEQ ID NO: 18, or SEQ ID NO: 20;

b) a complementary strand of a);

c) a fragment of a) or b) comprising at least 20 nucleotides; and d) a sequence that is degenerate as a result of the genetic code to any one of the sequences as defined in a), b) or c).

The present invention further relates to an expression vector comprising the above defined polynucleotide sequence.

The present invention further relates to novel hosts transformed with the vectors of the invention, especially hosts that are capable of high level expression of the endoglucanase or endoglucanase fusion protein of the invention.

The present invention further relates to an enzyme preparation, which contains one or more endoglucanases or endoglucanase fusion proteins of the invention.

The present invention further relates to methods for using the enzyme preparations of the invention for the biofinishing of textiles, especially for depilling.

The present invention further relates to methods for using the enzyme preparations of the invention for the finishing of textiles, especially for biostoning of denim.

The present invention further relates to the use of the enzyme preparations of the invention in detergent compositions.

DETAILED DESCRIPTION OF THE INVENTION

Figure 1:
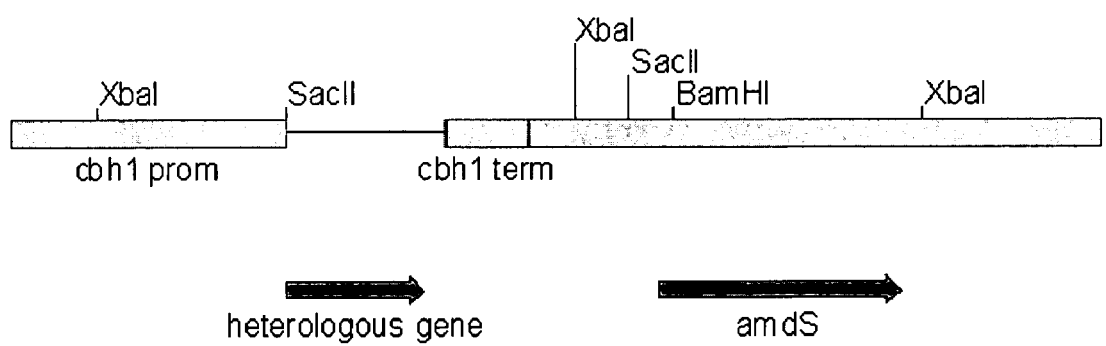
FIG. 1 illustrates the schematic picture of the expression cassettes used in the transformation of *Trichoderma reesei* protoplasts for production of *Acremonium thermophilum* cellulases of the invention. The recombinant genes were under control of *T. reesei* cbhI/cer/7A promoter (cbhI prom) and transcription termination was ensured with the addition of the *T. reesei* cbhI terminator (cbhI term). The amdS gene (amdS) was included for selection of the transformants.

The present invention is based on efforts to find further improved cellulases for use in textile industry. Surprisingly it was found that, starting from an *Acremonium* species, novel endoglucanases could be isolated and recombinant enzymes could be produced, which endoglucanases not only have an acceptable temperature profile but also show unexpected favorable depilling performance and are at least four times as efficient as a commercial EG-containing preparation. Additionally, the novel endoglucanases showed excellent biostoning properties as compared to prior art cellulases.

Accordingly, the present invention relates to an endoglucanase polypeptide comprising a fragment having cellulolytic activity and being selected from the group consisting of:

a) a polypeptide comprising an amino acid sequence having at least 78% identity to SEQ ID NO: 2 or an amino acid sequence having at least 68% identity to SEQ ID NO: 4, b) a variant of a) comprising a fragment having cellulolytic activity; and c) a fragment of a) or b) having cellulolytic activity.

In one preferred embodiment of the invention said amino acid has at least 80%, preferably 85%, more preferably 90%, still more preferably 95%, most preferably 98% identity to SEQ ID NO: 2.

In another preferred embodiment of the invention said amino acid has at least 70%, preferably 75%, more preferably 80%, still more preferably 85%, still more preferably 90%, most preferably 95% identity to SEQ ID NO: 4.

In yet another preferred embodiment of the invention said amino acid has SEQ ID NO: 2 or SEQ ID NO: 4.

In yet another preferred embodiment of the invention said variant has the amino acid sequence of SEQ ID NO: 17 or SEQ ID NO: 19.

In yet another preferred embodiment of the invention the polypeptides are obtainable or originate from an *Acremonium* sp., preferably from *Acremonium thermophilum*.

The present invention also relates to an endoglucanase fusion protein comprising an amino acid sequence derived from a polypeptide comprising an amino acid sequence having at least 68% identity to SEQ ID NO: 4 attached to a cellulose binding domain (CBD).

In one preferred embodiment of the invention said fusion protein comprises additionally comprises a linker region.

In another preferred embodiment of the invention said fusion protein comprises an amino acid sequence of SEQ ID NO: 4 attached to a CBD derived from a polypeptide comprising an amino acid sequence having SEQ ID NO: 2.

In yet another preferred embodiment of the invention said endoglucanase fusion protein has SEQ ID NO: 21.

The present invention further relates to an isolated polynucleotide encoding the above defined endoglucanase polypeptide.

Specifically in one embodiment of the invention the isolated polynucleotide has a nucleotide sequence selected from the group consisting of:

a) a nucleotide sequence of SEQ ID NO:1, SEQ ID NO:3, SEQ ID NO: 16, SEQ ID NO: 18, or SEQ ID NO: 20;

b) a complementary strand of a);

c) a fragment of a) or b) comprising at least 20 nucleotides; and d) a sequence that is degenerate as a result of the genetic code to any one of the sequences as defined in a), b) or c).

The present invention further relates to an expression vector comprising the above defined polynucleotide sequence.

The present invention further relates to novel hosts transformed with the vectors of the invention, especially hosts that are capable of high level expression of the endoglucanase or endoglucanase fusion protein of the invention. According to a preferred embodiment of the invention the enzymes are obtainable from *Acremonium thermophilum* strain ALKO4245 deposited as CBS 116240.

The present invention further relates to an enzyme preparation, which contains one or more endoglucanases or endoglucanase fusion proteins of the invention.

The present invention further relates to methods for using the enzyme preparations of the invention for the biofinishing of textiles, especially for depilling.

The present invention further relates to methods for using the enzyme preparations of the invention for the finishing of textiles, especially for biostoning of denim.

The present invention further relates to the use of the enzyme preparations of the invention in detergent compositions.

The endoglucanase and endoglucanase fusion protein preparations of the invention are especially useful in the textile and detergent industry. They are especially useful in the textile industry for biofinishing of fabrics or garments, e.g., depilling, defuzzing, color clarification, harshness reduction, creation of different finishes (for example, a 'peach skin,' 'worn out,' 'sand washed,' or 'antique look' effect) and for biofinishing of yarn, for example, reduction of hairiness and improvement of smoothness. Additional uses include the use in detergent compositions to improve fabric care properties by antipilling, antigraying, color clarification and softening, and to improve textile-cleaning effect, for instance soil removal. Additional uses further include the use in biostoning of denim.

In cotton fabric, fuzz (microfibers) emerges from the surface, which may entangle during processing, thus forming pills. Enzymes weaken the microfibers raising up from the surface and shear forces of the treatment then remove them (Nierstrasz and Warmoeskerken, 2003). As used in the present context the expression "biofinishing" (also called depilling, defuzzing or biopolishing) refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability, which may improve also the dyeability. Cellulase enzymes are used for treating or finishing of cellulose-containing textile materials, such as cotton, flax, ramie, jute, viscose, modal, lyocell and cupro, or blends thereof.

As used in the present context the expression "biostoning" of fabric or garment means the use of enzymes in place of, or in addition to, pumice stones for the treatment of fabric or garment, especially denim.

As used in the present context the expression "backstaining" refers to the tendency of released dye to redeposit on the surface of the fabric fibers.

As used in the present context the expression "detergent" refers to a cleansing agent that can contain surface active agents (anionic, non-ionic, cationic and ampholytic surfactants), builders and other optional ingredients such as anti-redeposition and soil suspension agents, optical brighteners, bleaching agents, dyes and pigments and hydrolases. Suitable listing of the contents of detergents is given in U.S. Pat. No. 5,433,750, a suitable list of surfactants is given in U.S. Pat. No. 3,664,961.

The biological activity of an endoglucanase is its catalytic activity, and/or its ability to bind to cellulosic material. Cellulolytic activity of an endoglucanase is its hydrolytic activity.

As used in the present context the expression "*Acremonium* sp." refers to a filamentous fungal genus having the characteristics of the strain CBS 116240.

An expression vector is a cloning plasmid or vector capable of expressing DNA encoding the endoglucanases and endoglucanase fusion proteins of the invention after transformation into a desired host. When a fungal host is used, the gene of interest is preferably provided to a fungal host as part of a cloning or expression vehicle that integrates into the fungal chromosome, or allows the gene of interest to integrate into the host chromosome, or as an autonomously replicating plasmid. Sequences that are part of the cloning vehicle or expression vehicle may also be integrated with said DNA during the integration process. In addition, in fungi the expression vector or parts thereof can be targeted into predetermined loci.

The DNA encoding the endoglucanases and the endoglucanase fusion proteins of the invention is also preferably placed under the control of (i.e., operably linked to) certain control sequences such as promoter sequences provided by the vector (which integrate with the gene of interest). Alternatively, the control sequences can be those at the insertion site.

The expression control sequences of an expression vector will vary depending on whether the vector is designed to express a certain gene in a prokaryotic or in a eukaryotic host (for example, a shuttle vector may provide a gene for selection in bacterial hosts). Expression control sequences can contain transcriptional regulatory elements such as promoters, enhancer elements, and transcriptional termination sequences, and/or translational regulatory elements, such as translational initiation and termination sites.

A polynucleotide molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a promoter region sequence linked to the 5' end of the protein encoding sequence) are said to be operably linked if function of promoter results in the transcription.

The vectors of the invention may further comprise other operably linked regulatory elements, such as enhancer sequences.

In a preferred embodiment, genetically stable transformants are constructed whereby the DNA encoding the endoglucanases or endoglucanase fusion proteins of the invention is integrated into the host chromosome by transformation with a vector, which harbors sequences promoting integration of said vector into the chromosome.

Cells that have stably integrated DNA encoding the endoglucanases or the endoglucanase fusion proteins of the invention into their chromosomes are selected by also introducing one or more markers, homologous or heterologous, which allow for selection of host cells which contain the expression vector in the chromosome, for example the marker may provide biocide resistance, e.g., resistance to antibiotics, or heavy metals, such as copper, or markers complementing an auxotrophic mutation in the host chromosome, and the like. The selectable marker gene can either be directly linked to the DNA gene sequences to be expressed, or introduced into the same cell by co-transformation.

Once the vector or DNA sequence of the invention containing the construct(s) is prepared for expression, the DNA construct(s) is introduced into an appropriate host cell by any of a variety of suitable means, including transformation as known in the art. After the introduction of the vector, recipient cells are grown in a selective medium, which selects for the growth of transformed cells.

Suitable expression and production host systems are for example the production system developed for the fungus host *Trichoderma* (EP 244 234), or *Aspergillus* production system, such as *A. oryzae* or *A. niger* (WO 9708325 and WO 9533386, U.S. Pat. No. 5,843,745, U.S. Pat. No. 5,770,418), or the production system developed for *Fusarium*, such as *F. oxysporum* (Malardier et al., 1989). Suitable production systems developed for bacteria are a production system developed for *Bacillus*, for example *B. subtilis* or for *E. coli*, or for actinomycete *Streptomyces*. Suitable production systems developed for yeasts are systems developed for *Saccharomyces, Shizosaccharomyces* or *Pichia pastoris*. Production systems in some other microbes or in mammalian cells or in plants are also possible.

Expression of the cloned gene sequence(s) results in the production of the desired protein, or in the production of a fragment of this protein. This expression can take place in a continuous manner in the transformed cells, or in a controlled manner.

Fragments are understood to be parts of polypeptide or nucleic acid molecules long enough to have the desired enzymatic properties or to code for the described endoglucanases or endoglucanase fusion proteins or a biologically active fragment thereof. The term "derivative" means in this context that the nucleotide sequences of these molecules differ from the sequences of the above-described nucleic acid molecules in one or more positions and are highly homologous to said sequence.

As used in the present context the term "identity" refers to the global identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite; Rice et al., 2000) program package, version 3.0.0, with the following parameters: EMBLOSUM62, Gap penalty 10.0, Extend penalty 0.5. The algorithm is described in Needleman and Wunsch (1970). The man skilled in the art is aware of the fact that results using Needleman-Wunsch algorithm are comparative only when aligning corresponding domains of the sequence. Consequently comparison of e.g. cellulase sequences including CBD or signal sequences with sequences lacking those elements cannot be done.

Cellulolytic enzymes useful for hydrolyzing cellulosic material are obtainable or originate from *Acremonium* sp., preferably *A. thermophilum*. "Obtainable from" or "originating from" means that they can be obtained from said species, but it does not exclude the possibility of obtaining them from other sources. In other words they may originate from any organism including plants. Preferably they originate from microorganisms e.g. bacteria or fungi. The bacteria may be for example from a genus selected from *Bacillus, Azospirillum* and *Streptomyces*. More preferably the enzyme originates from fungi (including filamentous fungi and yeasts), for example from a genus selected from the group consisting of *Thernoascus, Acremonium, Chaetomium, Achaetomium, Aspergillus, Botrytis, Chrysosporium, Collybia, Fomes, Fusarium, Humicola, Hypocrea, Lentinus, Melanocarpus, Myceliophthora, Myriococcum, Neurospora, Penicillium, Phanerochaete, Phlebia, Pleurotus, Podospora, Polyporus, Rhizoctonia, Scytalidium, Pycnoporus, Trametes* and *Trichoderma*.

As used in the present context the expressions "enzyme preparation", "cellulase preparation" and "endoglucanase preparation" refer to any enzyme product, which contains at least one endoglucanase or endoglucanase fusion protein of the invention. Thus, such an enzyme preparation may be a spent culture medium or filtrate containing one or more endoglucanases or endoglucanase fusion proteins or one or more endoglucanases or endoglucanase fusion proteins and other enzymes, an isolated endoglucanase or endoglucanase fusion protein or a mixture of one or more endoglucanases or endoglucanase fusion proteins or a mixture of one or more endoglucanases or endoglucanase fusion proteins and one or more other enzymes. In addition to the endoglucanase activity, such a preparation may contain additives, such as stabilizers, buffers, preservatives, surfactants and/or culture medium components. Preferred additives are such, which are commonly used in enzyme preparations intended for the application, where the enzyme preparation is used. The enzyme preparation may be in the form of liquid, powder or granulate.

By "spent culture medium" is here meant the culture medium of the host comprising the produced enzymes. Preferably the host cells are separated from the said medium after the production.

The enzyme preparation may comprise one or more endoglucanases or endoglucanase fusion proteins of the present invention or other cellulase enzymes together with one or more endoglucanases or endoglucanase fusion proteins of the present invention. For example, endoglucanases having different properties may be combined to make the enzyme preparation more useful for different conditions.

To obtain the enzyme preparations of the invention, the hosts having the desired properties (that is, hosts capable of expressing economically feasible quantities of the endoglucanases or endoglucanase fusion proteins of the invention) are cultivated under suitable conditions, the desired enzymes are secreted from the hosts into the culture medium, and the enzyme preparation is recovered from said culture medium by methods known in the art.

The enzyme preparation may comprise, in addition to the endoglucanase or the endoglucanase fusion protein, one or more other enzymes, which may be for example amylases, lipases, proteases, pectinases and/or oxidases, such as laccases and peroxidases. Alternatively, before, during or after the treatment with the endoglucanase or the endoglucanase fusion protein of the present invention, another enzyme treatment may be carried out. The enzyme treatment may comprise, for example, one or more amylase treatments, one or more cellulase treatments and/or one or more peroxidase and/or laccase treatments. Which other enzymes are included to the enzyme preparation or are used in the enzyme treatment, depends on the application.

The enzyme preparation can be the culture medium with or without the native or transformed host cells, or is recovered from the same by the application of methods well known in the art. However, because the endoglucanases or the endoglucanase fusion proteins of the invention are secreted into the culture media and display activity in the ambient conditions of the cellulolytic liquor, it is an advantage of the invention that the enzyme preparations of the invention may be utilized directly from the culture medium with no further purification. If desired, such preparations may be lyophilized or the enzymatic activity otherwise concentrated and/or stabilized for storage. The enzyme preparations of the invention are very economical to provide and use because (1) the enzymes may be used in a crude form; isolation of a specific enzyme from the culture medium is unnecessary and (2) because the enzymes are secreted into the culture medium, only the culture medium need be recovered to obtain the desired enzyme preparation; there is no need to extract an enzyme from the hosts. Preferably the host for such production is *Trichoderma*, and especially *T. reesei*.

The enzyme preparations of the invention may be provided as a liquid or as a solid, for example, in a dried powder or granular or liquid form, especially non-dusting granules, or a stabilized liquid, or the enzyme preparation may be otherwise concentrated or stabilized for storage or use. It is envisioned that enzyme preparations containing one or more of the cellulases of the invention can be further enriched or made partially or completely deficient in specific enzymatic activities, so as to satisfy the requirements of a specific utility in various applications e.g. in the textile industry. A mixture of enzyme activities secreted by a host and especially a fungal host can be chosen to be advantageous in a particular industrial application, for example biofinishing and biostoning.

The enzyme preparations of the invention can be adjusted to satisfy the requirements of specific needs in various applications in the textile, detergent or the pulp and paper industry.

Blends may be prepared with other macromolecules that are not necessarily all produced from the same host (for example, other enzymes such as endoglucanases, amylases, lipases, proteases, pectinases and/or oxidases, such as laccases and peroxidases) or chemicals that may enhance the performance, stability, or buffering of the desired enzyme preparation. Non-dusting granules may be coated. Liquid enzyme preparations can be stabilized by adding a polyol such as propylene glycol, a sugar or sugar alcohol, lactic acid or boric acid, or sodium chloride, according to established methods.

Protected forms of the enzymes of the invention may be prepared as described in EP 238,216.

The enzyme preparations of the invention can contain a surfactant which can be anionic, non-ionic, cationic, amphoteric or a mixture of these types, especially when used as a detergent composition. Useful detergent compositions are described e.g. in WO 94/07998, U.S. Pat. No. 5,443,750 and U.S. Pat. No. 3,664,961.

If required, a desired enzyme may be further purified in accordance with conventional conditions, such as extraction, precipitation, chromatography, affinity chromatography, electrophoresis, or the like.

The enzyme preparations of this invention are especially useful in textile industry preferably in biofinishing and in biostoning or in detergent industry. Other useful areas are in pulp and paper industry.

"Biofinishing" refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability and which may improve also the dyeability.

Enzymatic depilling can be carried out at any stage during textile wet processing, preferably after desizing and bleaching. The enzymatic process requires equipment with sufficient shear forces and mixing such as jet winch or washing machine (Nierstrasz V. A. and Warmoeskerken M. M. C. G., 2003).

Biofinishing is typically performed at about pH 4.0–6.0. The temperature of the reaction can range from about 30° C.

to 70° C., and is preferably 50–60° C. The liquor ratio (the ratio of the volume of liquid per weight of fabric) may range from about 3:1 to 20:1, preferably 5:1 to 10:1. The incubation time is generally 15 to 90 minutes, preferably 30 to 60 min. The enzyme dosage depends greatly on the type of the fabrics, machinery, process conditions (pH, temperature, liquor ratio, treatment time, denim load, process scale) and type of enzyme preparation and like. A person skilled in art is capable in defining suitable dosages and conditions.

The endoglucanases and endoglucanase fusion proteins of the invention are especially useful in the textile industry for biofinishing of fabrics or garments e.g. depilling, defuzzing, color clarification, harshness reduction, the creation of different finishes (for example, a 'peach skin,' 'worn out,' 'sand washed,' or 'antique look' effect) and biofinishing of yarn (for example reduction of hairiness, improvement of smoothness). The endoglucanases and endoglucanase fusion proteins of the present invention can be used in biofinishing in acid and in neutral conditions.

The endoglucanases and endoglucanase fusion proteins of the present invention are useful in detergent compositions to improve fabric care properties by antipilling, antigraying, color clarification and softening, and to improve textile cleaning effect, for instance soil removal.

Stone washing has three steps: desizing, abrasion and after-treatment. The first step, desizing process is normally the first wet treatment of jeans and means the removal of starch or other sizing agents applied usually to the warp yarns to prevent damage during the weaving process. Alpha-amylases are used to remove starch-based size for improved and uniform wet processing. After desizing the jeans are normally rinsed with water or continued directly with the abrasion step.

The second step, abrasion, can be performed with enzymes or pumice stones or both. In all cases mechanical action is needed to remove the dye, and the treatment is usually carried out in washing machines, like drum washers. The term "abraded" means herein the appearance of denim fabric when it has been treated by cellulase enzymes or stones, or both. As a result of un-even dye removal there are contrasts between dyed areas and areas from which dye has been removed. Synonymous expressions are "stone washed look" or "worn look". In enzymatic stone washing, or biostoning, abrasion with pumice stones is completely or partially eliminated and cellulase is added to facilitate the abrasion of Indigo dye from the fiber surface. The cellulase treatment may be done using neutral or acid cellulases or both.

Abrasion is generally followed by the third step, after-treatment that includes washing and rinsing steps during which detergents, optical brighteners or softeners may be used. After the enzymatic treatment the reaction must be stopped in order to prevent damage of the treated materials, for example by temperature and/or pH inactivation, the latter comprising a thorough rinsing and/or detergent wash-off. This ensures that the mechanical strength of the fiber is not further compromised by the continued presence of the enzyme.

By "denim" is meant, in connection of this invention, denim fabric, usually denim garments, particularly jeans. Advantageously the denim is Indigo dyed denim. Denim can also be treated with Indigo, with derivatives of Indigo or denim dyed with Indigo together with some other dye, for example Indigo-dyed denim with sulphur bottom.

Treatment with a cellulase(s) can completely replace treatment with pumice stones (for example, 1 kg commercial enzyme vs. 100 kg stones). However, cellulase treatment can be combined with pumice stone treatment when it is desired to produce a heavily abraded finish. A peach skin effect in which a fine protruding hair-like covering is created is also achieved by a wash combining a neutral cellulase with pumice stones. The cellulases of this invention are especially useful to provide abraded look and to minimize backstaining in biostoning.

Biostoning is typically performed at about pH 3.0–8.0, and preferably at pH 4.0–6.0. The temperature of the reaction can range from about 30° C. to 70° C. and is preferably between 50–60° C. The liquor ratio (the ratio of the volume of liquid per weight of fabric) may range from about 3:1 to 20:1, preferably 5:1 to 10:1. The treatment time can range between 15 min–90 min and preferably 30 min–60 min. It should be emphasized that the enzyme dosage depends greatly on the type of the fabrics, machinery, process conditions (pH, temperature, liquor ratio, treatment time, denim load, process scale) and type of enzyme preparation and like. If desired, pumice stones can be used in combination with the endoglucanases or endoglucanase fusion proteins. The enzyme dosage required will then be significantly lower. A person skilled in art is capable in defining suitable dosages and conditions.

The textile material that is treated with the enzyme preparations of the invention may be manufactured of natural cellulose containing fibers or manmade cellulose containing fibers or mixtures thereof. Examples of natural cellulosics are cotton, linen, hemp, jute and ramie. Examples of manmade cellulosics are viscose, cellulose acetate, cellulose triacetate, rayon, cupro and lyocell. The above-mentioned cellulosics can also be employed as blends of synthetic fibers such as polyester, polyamide or acrylic fibers. The textile material may be yarn or knitted or woven or formed by any other means.

The endoglucanases and endoglucanase fusion proteins of the present invention, besides being especially useful for the treatment of fabric, are useful in general in any area requiring cellulase activity.

In the pulp and paper industry, cellulases can be used, for example, in deinking or modifying fiber of different recycled papers and paperboards having neutral or alkaline pH, in improving the fiber quality, or increasing the drainage in paper manufacture. Other examples include the removal of printing paste thickener and excess dye after textile printing, and as a treatment for animal feed. For example, if the intended application is improvement of the strength of the mechanical pulp, then the enzyme preparations of the invention may provide one or more of these proteins so as to enhance or facilitate the ability of cellulose fibers to bind together. In a similar manner, in the application of pulp refining, the endoglucanases and endoglucanase fusion protein preparations of the invention may provide one or more of these proteins at a level that enhance or facilitate such swelling.

The endoglucanases and endoglucanase fusion proteins of the present invention provide unexpected advantages when used in textile industry and especially in biofinishing, such as depilling, and in biostoning. The endoglucanases and endoglucanase fusion proteins of the present invention are considerably more efficient than the cellulases of prior art. In biofinishing at least four-fold lower dosages could be used. In other words, higher performance is achieved by using the endoglucanases and endoglucanase fusion proteins of the present invention. In depilling the endoglucanases and endoglucanase fusion proteins of the present invention were more efficient and produced a stable smooth surface.

The invention is described in more detail in the following examples, which are not be interpreted to narrow the scope of the invention but only to clarify the use of the invention.

EXAMPLE 1

Cultivation of the *Acremonium thermophilum* ALKO4245

The *Acremonium thermophilum* strain ALKO4245 was grown in a 2 liter bioreactor (Braun Biostat® B, Braun, Melsungen, Germany) in the following medium, g/l: Solka Floc cellulose 40, corn steep powder 15, distiller's spent grain 5, oats spelt xylan 3, locust bean gum 3, $(NH_4)_2SO_4$ 5 and $KH_2PO_4$ 5. The pH range was 5.2±0.2 ($NH_3/H_2SO_4$), aeration 1 vvm, stirring 300–600 rpm, antifoam control with Struktol® and the temperature 42° C. The cultivation time was 4 days. After cultivation the cells and other solids were collected by centrifugation and the supernatant was recovered.

EXAMPLE 2

Purification of an endoglucanase from *Acremonium thermophilum* ALKO4245

The culture supernatant of *Acremonium thermophilum* ALKO4245, grown as described in Example 1, was incubated at 70° C. for 24 hours after which it was concentrated by ultrafiltration. The pure endoglucanase was obtained by sequential purification with hydrophobic interaction and cation exchange chromatography followed by gel filtration. The endoglucanase activity of the fractions collected during purification was determined using carboxymethyl cellulose (CMC) as a substrate (according to the procedure of IUPAC, 1987).

The concentrated culture supernatant was applied to the HiPrep 16/10 Butyl FF hydrophobic interaction column (GE Healthcare) equilibrated with 20 mM potassium phosphate buffer, pH 6.0, containing 1 M $(NH_4)_2SO_4$. Bound proteins were eluted with a linear gradient from the above buffer to 5 mM potassium phosphate, pH 6.0. Fractions were collected and the endoglucanase activity was determined as described above. The endoglucanase activity eluted in a broad conductivity area of 120 to 15 mS/cm.

Combined fractions were applied to the HiTrap SP XL cation exchange column (GE Healthcare) equilibrated with 8 mM sodium acetate, pH 4.5. Bound proteins were eluted with a linear gradient from 0 to 0.25 M NaCl in the equilibration buffer. The protein containing endoglucanase activity eluted at the conductivity area of 3–7 mS/cm. Cation exchange chromatography was repeated and the protein eluate was concentrated by freeze drying.

The dissolved sample was loaded onto the Superdex 75 HR10/30 gel filtration column (Pharmacia) equilibrated with 20 mM sodium phosphate buffer, pH 7.0, containing 0.15 M NaCl. The main protein fraction eluted from the column with the retention volume of 13.3 ml. The protein eluate was pure as judged by SDS-polyacrylamide gel electrophoresis and the molecular weight was evaluated to be 40 kDa. The specific activity of the purified protein, designated as *Acremonium thermophilum* EG_40 or At EG_40 (SEQ ID NO: 2), at 50° C. was determined to be 450 nkat/mg (according to the procedure of IUPAC, 1987, supra, using CMC as a substrate).

The thermal stability of the purified endoglucanase was determined at different temperatures. The reaction was performed in the presence of 0.1 mg/ml BSA at pH 5.0 for 60 min using CMC as a substrate. At EG_40 was stable up to 80° C. The *T. reesei* reference enzymes EGI (Cel7B) and EGII (Cel5A) retained 100% of their activity up to 60° C. and 65° C., respectively.

For internal amino acid sequencing, the purified *Acremonium thermophilum* ALKO4245 EG_40 protein (SEQ ID NO: 2) was first alkylated and digested into tryptic peptides. Generated-peptides were desalted and partially separated by nano liquid chromatography (reverse-phase). The internal peptides were sequenced by electrospray ionization combined to tandem mass spectrometry (ESI-MS/MS) using the Q-TOF1 (Waters Micromass®) instrument. The internal peptide sequences so obtained are listed in Table 1.

TABLE 1

Internal peptide sequences determined from the *Acremonium thermophilum* EG_40 cellulase

| Peptide | Sequence | SEQ ID NO: |
|---|---|---|
| Peptide 1 | QSCSSFPAPLKPGCQWR | 5 |
| Peptide 2 | YALTFNSGPVAGK | 6 |
| Peptide 3 | VQCPSELTSR | 7 |
| Peptide 4 | NQPVFSCSADWQR | 8 |
| Peptide 5 | YWDCCKPSCGWPGK | 9 |
| Peptide 6 | PTFT | 10 |

EXAMPLE 3

Cloning of *Acremonium thermophilum* (ALKO4245) cel45A and cel45B Genes

Standard molecular biology methods were used in the isolation and enzyme treatments of DNA (plasmids, DNA fragments), in *E. coli* transformations, etc. The basic methods used are described in the standard molecular biology handbooks, e.g. Sambrook, J., et al., 1989 and Sambrook J. and Russell, D. W., 2001.

The genomic library of *Acremonium thermophilum* ALKO4245 was constructed in Lambda DASH®II vector (Stratagene, USA) according to the instructions from the manufacturer. The chromosomal DNA, isolated by the method of Raeder and Broda, 1985, was partially digested with Sau3A. The digested DNA was size-fractionated in an agarose gel and the fragments of chosen size (about 5–23 kb) were isolated, dephosphorylated and ligated to the BamHI digested lambda vector arms. The ligation mixture was packaged using the Gigapack III Gold packaging extracts according to the manufacturer's instructions (Stratagene, USA). The titer of the genomic library was $3.7 \times 10^5$ pfu/ml and that of the amplified library was $4.2 \times 10^8$ pfu/ml.

The internal peptide sequences from the purified *Acremonium thermophilum* EG_40 cellulase obtained as described in Example 2 shared homology with cellulases of the glycosyl hydrolase family 45, such as *Thielavia terrestris* endoglucanase (GenBank Accession No. CQ827970) and *Melanocarpus albomyces* Cel45A cellulase (GenBank Accession No. AJ515703). In order to amplify a probe for screening of the *A. thermophilum* EG_40 encoding gene (cel45A; SEQ ID NO: 1) from the genomic library, degenerate primers were designed on the basis of the peptide sequences listed in Table 1 (Example 2). The order of the peptides in the protein sequence and the corresponding sense or anti-sense nature of the primers was deduced from the comparison with the homologous *M. albomyces* Cel45A sequence. The sense primer (TAYTGGGAYTGYT- GYAARCC, SEQ ID NO: 11) is based on amino acids 1 to 6 of peptide 5 (SEQ ID NO: 9) and the anti-sense primer (RTTRTCNGCRTTYTGRAACCA, SEQ ID NO: 12) is based on a peptide sequence (WFQNADN; SEQ ID NO: 13) of the homologous *M. albomyces* Cel45A protein. The PCR reaction mixtures contained 50 mM Tris-HCl, pH 9.0, 15 mM (NH$_4$)$_2$SO$_4$, 0.1% Triton X-100, 1.5 mM MgCl$_2$, 0.1 mM dNTPs, 0.5 µg of each primer, 1 unit of Dynazyme EXT DNA polymerase (Finnzymes, Finland), and approximately 0.5 µg of *Acremonium* genomic DNA. The conditions for PCR reactions were as follows: 5 min initial denaturation at 95° C., followed by 30 cycles of 1 min at 95° C., 1 min annealing at 50–60° C., 2 min extension at 72° C. and a final extension at 72° C. for 10 min. The extension products were examined in an agarose gel.

Two PCR products were obtained from the *Acremonium* PCR reaction. DNA fragments of about 0.6 kb (SEQ ID NO: 14) and 0.8 kb (SEQ ID NO: 15) were isolated from the agarose gel and cloned into the pCR4-TOPO® TA vector (Invitrogen, USA) resulting in plasmids pALK1710 and pALK1711, respectively. The cloned PCR products were characterized by sequencing and by performing Southern blot hybridizations (as described below) to the genomic *Acremonium* DNA digested with several restriction enzymes. The hybridization patterns obtained with the two fragments in stringent washing conditions suggest that two putative endoglucanase genes could be screened from the *Acremonium* genomic library. The deduced amino acid sequences of both PCR products have homology to several published endoglucanase sequences of glycosyl hydrolase family 45 (BLAST program, National Center for Biotechnology Information; Altschul et al., 1990).

The insert from plasmid pALK1710 and pALK1711 was isolated by restriction enzyme digestion and labeled with digoxigenin according to the manufacturer's instructions (Roche, Germany). About 1–2×10$^5$ plaques from the amplified *Acremonium* genomic library were transferred on nitrocellulose filters and screened by hydridization using digoxigenin-labeled inserts. The temperature for hybridization was 68° C. and the filters were washed 2×5 min at RT using 2×SSC—0.1% SDS followed by 2×15 min at 68° C. using 0.1×SSC–0.1% SDS. Several positive plaques were obtained, of which five strongly hybridizing plaques were purified from both screenings. Phage DNAs were isolated and analyzed by Southern blot hybridization. Restriction fragments of phage DNAs hybridizing to the probes were subcloned into the pBluescript II KS+ vector (Stratagene, USA) and the relevant parts were sequenced. In both cases the subcloned phage fragment contains the full-length gene of interest.

Table 2 summarizes the information of the probes used for screening of the endoglucanase genes, phage clones from which the genes were isolated, chosen restriction fragments containing the full-length genes with their promoter and terminator regions, names of plasmids containing the subcloned phage fragment, and the deposit numbers in the Deutsche Sammlung von Mikroorganismen und Zellkulturen GmbH culture collection (DSM) for *E. coli* strains carrying these plasmids. The depositions were made under the Budabest Treaty on 13.5. 2005.

TABLE 2

Probes used for cloning of the endoglucanase genes, phage clones and the subclones chosen, plasmid names and the corresponding deposit number of the *E. coli* strains

| Gene | Genomic library | Probe used in screening | Phage clone | Subcloned fragment | Plasmid | E.coli deposit no. |
|---|---|---|---|---|---|---|
| At cel45A | *A. thermophilum* ALKO4245 | pALK1710 | P24 | 5.5 kb SmaI | pALK1908 | DSM 17324 |
| At cel45B | *A. thermophilum* ALKO4245 | pALK1711 | P41 | 6.0 kb XhoI | pALK1904 | DSM 17323 |

Relevant information of the two genes, designated as At cel45A (SEQ ID NO: 1) and At cel45B (SEQ ID NO:3), is summarized in Table 3 and of the respective deduced protein sequences, At EG__40 (SEQ ID NO: 2) and At EG__40_like (SEQ ID NO: 4), in Table 4. The peptide sequences of the purified Acremonium EG__40 endoglucanase were found in the corresponding deduced amino acid sequence of the cloned gene confirming that an appropriate gene was cloned.

The full-length At cel45A gene (SEQ ID NO: 1) is 1076 bp in length, interrupted by two introns of 59 bp and 123 bp, and codes for a 297 amino acid polypeptide At EG__40 (SEQ ID NO: 2). The putative signal peptide cleavage site is after Ala21, and the N-terminus of the mature protein begins with Leu22, the mature protein (including CBD) comprising amino acids 22 to 297 of SEQ ID NO: 2). The EG__40 cellulase has a C-terminal consensus cellulose binding domain harboring amino acids Lys265 to Leu297 of the full-length polypeptide. The predicted mature protein after signal peptide cleavage has a molecular weight and pI of 28625 Da and 4.79, respectively (prediction made using the Compute pI/MW tool at ExPASy server, Gasteiger et al., 2003). The protein has two putative N-glycosylation sites N-X-S/T (predicted using the program NetNGlyc 1.0, Gupta et al., 2004).

Correspondingly, The full-length At cel45B gene (SEQ ID NO:3) is 1013 bp in length, interrupted by two introns of 155 bp and 102 bp, and codes for a 251 amino acid polypeptide At EG__40_like (SEQ ID NO: 4). The putative signal peptide cleavage site is after Ala20, and the N-terminus of the mature protein begins with Gln21, the mature protein comprising amino acids 21 to 251 of SEQ ID NO: 4) The EG__40_like cellulase has no C-terminal consensus cellulose binding domain. The predicted mature protein after signal peptide cleavage has a molecular weight and pI of 23972 Da and 6.11, respectively (prediction made using the Compute pI/MW tool at ExPASy server, Gasteiger et al., 2003). The protein has two putative N-glycosylation sites N-X-S/T (predicted using the program NetNGlyc 1.0, Gupta et al., 2004).

TABLE 3

Summary of the endoglucanase genes isolated from *Acremonium thermophilum* ALKO4245

| Endoglucanase gene | Length with introns (bp)[a] | Coding region (bp)[b] | No of introns | Lengths of introns (bp) | SEQ ID NO: |
|---|---|---|---|---|---|
| At cel45A | 1076 | 891 | 2 | 59, 123 | 1 |

TABLE 3-continued

Summary of the endoglucanase genes isolated from *Acremonium thermophilum* ALKO4245

| Endo-glucanase gene | Length with introns (bp)[a] | Coding region (bp)[b] | No of introns | Lengths of introns (bp) | SEQ ID NO: |
|---|---|---|---|---|---|
| At cel45B | 1013 | 753 | 2 | 155, 102 | 3 |

[a]The STOP codon is included.
[b]The STOP codon is not included.

TABLE 4

Summary of the deduced endoglucanase sequences of *Acremonium thermophilum* ALKO4245. ss, signal sequence.

| Endoglucanase protein | No of aas | Length of ss NN/HMM[a] | CBD[b] | Predicted MW (Da, ss not incl)[c] | Predicted pI (ss not incl) | Putative N-glycosylation sites[d] | SEQ ID NO: |
|---|---|---|---|---|---|---|---|
| AtEG_40 | 297 | 21/21 | Yes; K265 to L297 | 28625 | 4.79 | 2 | 2 |
| AtEG_40_like | 251 | 20/20 | No | 23972 | 6.11 | 2 | 4 |

[a]The prediction on the signal sequence was made using the program SignalP V3.0 (Nielsen et al., 1997; Bendtsen et al., 2004); the NN value was obtained using neural networks and HMM value using hidden Markov models.
[b]Presence of a cellulose binding domain in the protein, the amino acids of the C-terminal CBD are indicated (numbering according to the full length polypeptide).
[c]The predicted signal sequence is not included. Prediction was made using the Compute pI/MW tool at ExPASy server (Gasteiger et al., 2003).
[d]The putative N-glycosylation sites N-X-S/T were predicted using the program NetNGlyc 1.0 (Gupta et al., 2004, In preparation; www.cbs.dtu.dk/services/NetNGlyc/).

The deduced protein sequences of the *A. thermophilum* EG_40 and EG_40_like cellulases are similar to cellulases of glycosyl hydrolase family 45 (Table 5). The closest sequence homologies found for EG_40/Cel45A and EG_40_like/Cel45B were endoglucanase sequences of *Thielavia terrestris* (GenBank Accession No. CQ827970) and *Myceliophthora thermophila* (GenBank Accession No. AR094305), respectively. The alignments were performed using the Needle program of the EMBOSS program package.

TABLE 5

Comparison of the deduced protein sequences of the *Acremonium thermophilum* EG_40 and EG_40_like cellulases with their homologous counterparts

| Organism, enzyme, and accession number | Identity (%) |
|---|---|
| *Acremonium thermophilum* EG_40 | |
| *Thielavia terrestris* EG45, CQ827970 | 77.3 |
| *Melanocarpus albomyces* Cel45, AJ515703 | 75.3 |
| *Neurospora crassa*, hypothetical XM_324477 | 68.9 |
| *Humicola grisea* var *thermoidea*, EGL3, AB003107 | 67.5 |
| *Humicola insolens* EG5, A23635 | 67.3 |
| *Myceliophtora thermophila* fam 45, AR094305 | 57.9 |
| *Acremonium thermophilum* EG_40_like | 53.7 |
| *Acremonium thermophilum* EG_40_like | |
| *Myceliophthora thermophila* fam 45, AR094305 | 66.9 |
| *Magnaporthe grisea* 70-15 hypothetical, XM_363402 | 61.9 |
| *Thielavia terrestris* EG45, CQ827970 | 56.8 |
| *Acremonium thermophilum* EG_40 | 53.7 |
| *Melanocarpus albomyces* Cel45, AJ515703 | 52.8 |

EXAMPLE 4

Production of *Acremonium thermophilum* EG_40 and EG_40_like Cellulases in *Trichoderma reesei*

Expression plasmids were constructed for production of the recombinant *A. thermophilum* EG_40/Cel45A and EG_40_like/Cel45B cellulases. Both genes (cel45A or cel45B), including their own signal sequence, were exactly fused to the *T. reesei* cbh1 (cel7A) promoter by PCR (Table 6). The cbh1 promoter, cbh1 terminator and amdS marker gene were included as described in Paloheimo et al. 2003, supra. The linear expression cassette (FIG. 1) was isolated from the vector backbone by restriction enzyme digestion, transformed into *T. reesei* A96, and transformants selected with acetamide as sole nitrogen source. The host strain lacks four major endogenous cellulases: CBHI/Cel7A, CBHII/Cel6A, EGI/Cel7B and EGII/Cel5A. The transformations were performed according to Penttilä et al, 1987, with the modifications described in Karhunen et al., 1993. The transformants were purified on selection plates through single conidia prior to sporulating them on potato extract agar.

TABLE 6

The expression cassettes constructed for production of *Acremonium thermophilum* EG40 and EG40_like cellulases in *Trichoderma reesei*. The schematic structure of the expression cassettes is described in FIG. 1.

| Endoglucanase | Expression plasmid | Size of the expression cassette[a] | Heterologous terminator[b] |
|---|---|---|---|
| At EG_40 | pALK1920 | 10.9 kb NotI | 156 bp (HindIII) |
| At EG_40_like | pALK1921 | 8.6 kb EcoRI | 282 bp (SspI) |

[a]The expression cassette for *T. reesei* transformation was isolated from the vector backbone by EcoRI or NotI digestion.
[b]The number of nucleotides after the STOP codon of the cloned gene that are included in the expression cassette are indicated. The restriction site at the 3'-region of the gene that was used in construction of the expression cassette is indicated in parenthesis.

The endoglucanase production of the transformants was analyzed from the culture supernatants of shake flask cultivations (50 ml). The transformants were grown for 7 days in a complex cellulose-inducing medium (Joutsjoki et al., 1993) buffered with 5% $KH_2PO_4$ at pH 5.5. The enzyme activity of the recombinant protein was measured from the culture supernatant as the release of reducing sugars from carboxymethylcellulose (2% CMC) at 50° C. in 50 mM Sitrate buffer pH 4.8 essentially as described by Bailey, M.

J. and Nevalainen, K. M. H., 1981; Haakana, H., et al, 2004. Production of the recombinant protein was also detected from the culture supernatant by SDS-polyacrylamide gel electrophoresis. EG__40-specific polyclonal antibodies were produced in rabbits (University of Helsinki, Finland). The expression of EG__40 cellulase was verified by Western blot analysis with anti-EG__40 antibodies using the ProtoBlot Western blot AP system (Promega). The genotypes of the chosen transformants were analyzed by Southern blotting using the expression cassette as a probe.

Figure 2A:
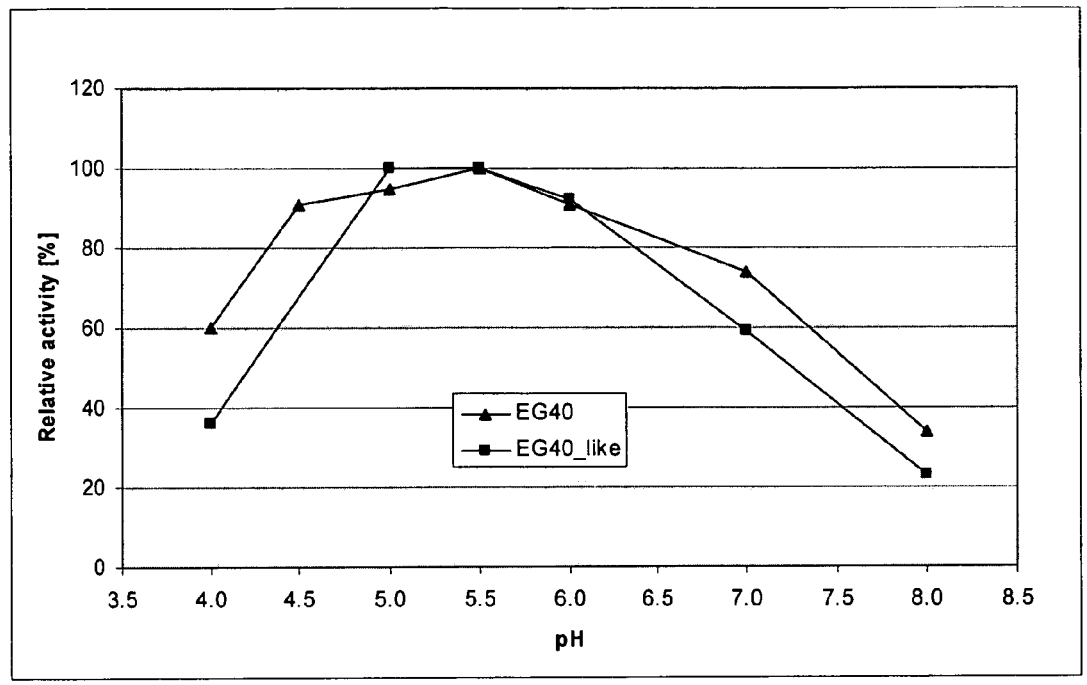
FIGS. 2A–2B illustrate the pH dependency of the heterologously produced *A. thermophilum* EG_40 and EG_40 like cellulases by determining from the culture supernatant using CMC as substrate in a 10 min reaction at 50° C. (A). The temperature optimum of EG_40 and EG_40 like cellulases was determined at pH 5.5 and 5, respectively. The reaction with CMC as a substrate was performed for 60 min. BSA (100 µg/ml) was added as a stabilizer. (B).
Figure 2B:
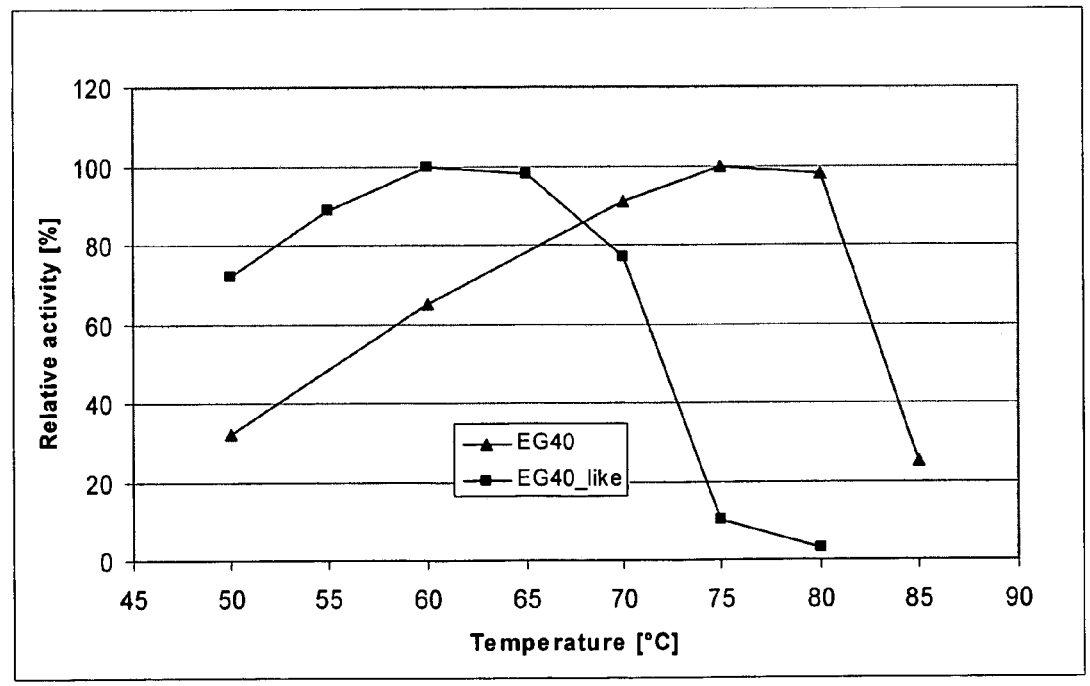

The pH optimum of the heterologously produced EG__40/Cel45A and EG__40_like/Cel45B cellulases was determined in the universal McIlvaine's buffer within a pH range of 4.0–8.0 using CMC as a substrate. As shown in FIG. 2A, the pH range of EG__40/Cel45A cellulase is relatively broad (4.5–6.0), the optimum being at pH 5.5. The pH optimum for EG__40_like/Cel45B was determined to be pH 5.0–5.5. The optimal temperature for enzymatic activity of EG__40/Cel45A and EG__40_like/Cel45B cellulases was determined to be 75–80° C. and 60° C., respectively (FIG. 2B). The thermal stability of the heterologously produced EG__40/Cel45A cellulase is comparable to that of the purified protein.

The chosen transformants RF6118 (At EG__40) and RF6071 (At EG__40_like) were cultivated in a 2 liter bioreactor for four days (28° C., pH 4.2) to obtain material for the application tests (see Examples 7 to 10).

EXAMPLE 5

Production of *Acremonium thermophilum* ALKO4245 EG__40 Cellulases Lacking Cellulose Binding Domain or Cellulose Binding Domain Plus the Linker Region To produce an *Acremonium thermophilum* ALKO4245 EG__40 cellulases lacking cellulose binding domain (CBD), At cel45A_CBDless, or the CBD plus the linker region, At cel45A_linkerCBDless, two cel45A deletion constructs are made; the first lacking the region coding for the CBD and the second additionally lacking the linker region between the catalytic core and the cellulose binding domain.

Standard molecular biology methods are used as described in Example 3. The 3'end of the cel45A gene is amplified by PCR. The antisense primer is designed to exclude the CBD or the linker+CBD region from the product and the PCR product is ligated to the 5'fragment of the cel45A gene to reconstitute full-length genes (SEQ ID NO: 16 and 18, respectively). Expression plasmids for the production of the CBDless and linkerCBDless versions of *A. thermophilum* EG__40/Cel45A cellulase are constructed and the recombinant proteins (SEQ ID NO: 17 and 19, respectively) are produced in *Trichoderma* as described in Example 4.

EXAMPLE 6

Production of the Recombinant *Acremonium thermophilum* ALKO4245 EG__40_like+CBD Fusion Protein To production of a recombinant *Acremonium thermophilum* ALKO4245 EG__40_like+CBD fusion protein (SEQ ID NO: 21), the cellulose binding domain (CBD) of the EG__40/Cel45A cellulase is linked to the EG__40_like cellulase. The construct contains the catalytic domain of EG__40_like (amino acids 1–242 of the full-length polypeptide) attached to the linker region and CBD of EG__40 cellulase (amino acids 235–297 of the full-length polypeptide).

Standard molecular biology methods are used as described in Example 3. First, a unique NruI restriction site near the C-terminal end of the EG__40_like sequence is introduced by PCR. This enables direct fusion of any blunt-ended DNA after amino acid S242 of the EG__40_like polypeptide. The linker+CBD region of the EG__40 encoding gene (cel45A) is amplified by PCR and a restriction fragment thereof ligated to the cel45B gene (after S242) to create At cel45B_cel45AlinkerCBD (SEQ ID NO: 20). Expression plasmid for production of the EG__40_likeCBD cellulase is constructed and the recombinant protein (SEQ ID NO: 21) produced in *Trichoderma* as described in Example 4.

EXAMPLE 7

Performance of EG__40 Cellulase Preparation in Denim Finishing at Different Temperatures

*Acremonium thermophilum* EG__40 cellulase from strain RF6118 produced using *Trichoderma reesei* as host as described in Example 4 was tested for its ability to create abraded look similar to that provided by pumice stones in biostoning of denim at different temperatures. A commercial EGII enriched preparation produced using *Trichoderma* as host (U.S. Pat. No. 5,874,293) efficient in denim finishing was used for comparison at 50° C.

Jeans made of Indigo dyed denim twill were used as test material after desizing with ECOSTONE® A200 alpha-amylase. The cellulase treatments were performed with Electrolux's Wascator FOM 71 CLS washer extractor under conditions described in Table 7.

The EGII enriched stabilized enzyme concentrate was dosed at 0.23% on the weight of the fabric, which is a typical dosage for the preparation in industrial applications. A concentrated and stabilized EG__40 preparation obtained from pilot fermentation was dosed at 0.18%. When calculated in terms of the protein content, the dosages were ca. 0.20 mg and 0.035 mg per g of fabric using the Bio-Rad Protein Assay Dye Reagent (BioRad, Hercules, Calif., USA) and bovine gammaglobulin as the standard. The cellulase enzyme was inactivated after draining by raising the pH above 11 through an addition of 5 g of NaOH (10 min. 40° C.) and rinsing three times. The jeans were dried in a tumbler.

The biostoning effect/abrasion level was evaluated by measuring the color as reflectance values with Minolta CM 2500 spectrophotometer using L*a*b* color space coordinates (illuminant D65/2°). The color from the face side and the reverse side of denim was measured after desizing (i.e. before the cellulase treatment) and after the cellulase treatment. Each measurement value on the face side of denim was an average of approximate 40 measurements. Two pairs of jeans were used in each test and the final result was the average of them. The results are shown in Table 8 and FIG. 3.

TABLE 7

The test conditions/process parameters used in cellulase treatments

| Process parameter | |
|---|---|
| Denim load | 1.3–1.4 kg |
| Water | 19 liter |
| pH control (pH 5–5.3) | 5 ml Acetic acid (80%) |
| Time | 45 min |
| Temperature | 40, 50, 60, or 70° C. |
| Cellulase dosage | 0.18% or 0.23% on the weight of the fabric |

TABLE 8

Color measurements of the face side of denim treated with EG_40 preparation at different temperatures

| Enzyme preparation | Dosage, % owf[a] | Protein mg/g fabric | Temp., ° C. | Before cellulase treatment L* | Before cellulase treatment b* | After cellulase treatment L* | After cellulase treatment b* | Increase of L* |
|---|---|---|---|---|---|---|---|---|
| EGII enriched conc. | 0.23 | 0.20 | 50 | 22.24 | −15.57 | 30.08 | −17.64 | 7.84 |
| EG40 conc., RF6118 | 0.18 | 0.035 | 70 | 21.88 | −15.54 | 31.07 | −16.76 | 9.20 |
| EG40 conc., RF6118 | 0.18 | 0.035 | 60 | 22.21 | −15.40 | 34.16 | −16.34 | 11.95 |
| EG40 conc., RF6118 | 0.18 | 0.035 | 50 | 22.00 | −15.22 | 30.10 | −17.26 | 8.10 |
| EG40 conc., RF6118 | 0.18 | 0.035 | 40 | 22.13 | −14.98 | 27.26 | −17.50 | 5.13 |

[a]on the weight of the fabric
Treatment with EGII enriched preparation was used for comparison at 50° C.
L* indicates the lightness, −b* is the blue direction, +b* is the yellow direction.

Figure 3:
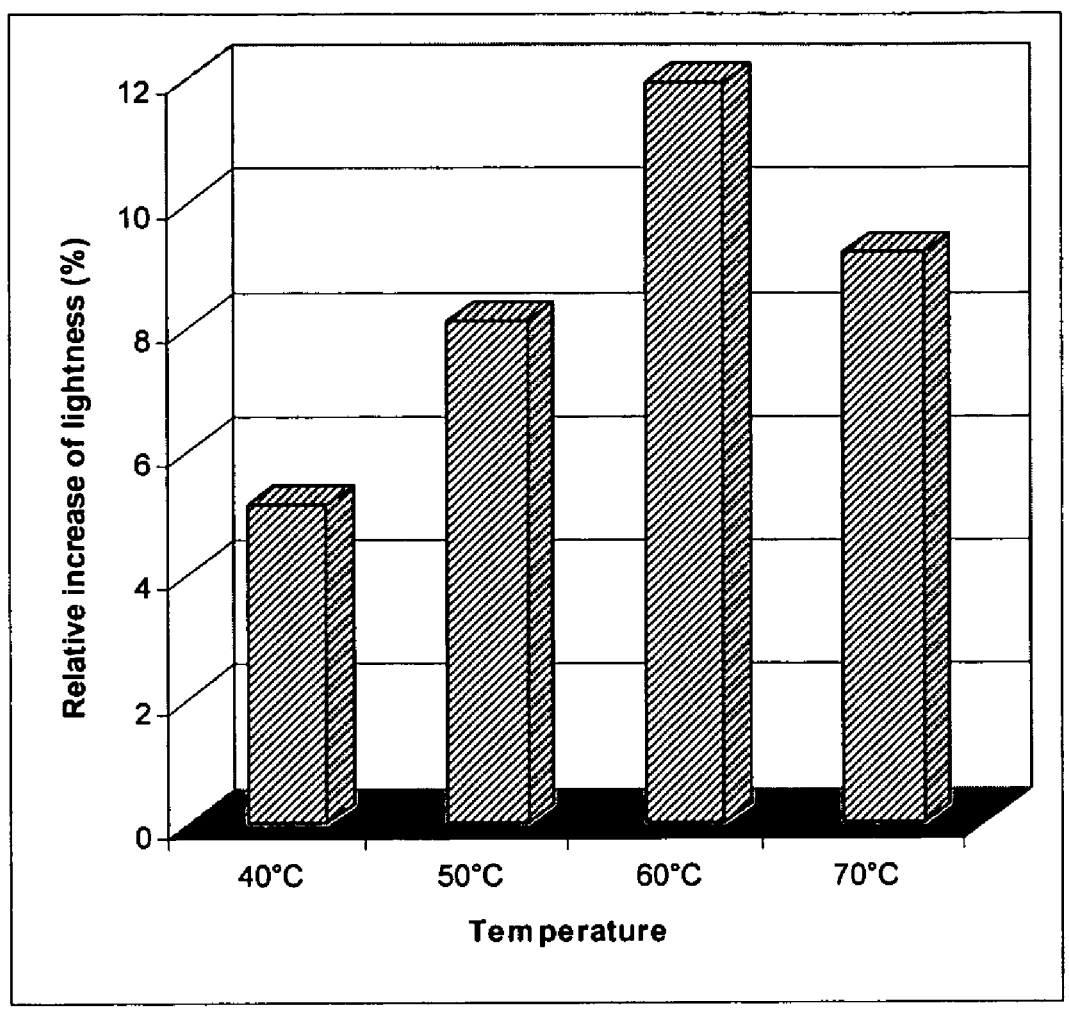
FIG. 3 shows the performance of EG_40 cellulase in biostoning at different temperatures evaluated by measuring the color.

Results in Table 8 and FIG. 3 show that the biostoning effect of EG_40 was very good at a low dosing range. With strain RF6118 similar abrasion level (lightness L*) compared to EGII enriched preparation was obtained at 50° C. with a 6 times lower amount of protein.

EXAMPLE 8

Boosting the Washing Performance of Egii Enriched Enzyme Preparation with EG_40 Cellulase in Denim Finishing The EGII enriched preparation was boosted with the EG_40 preparation (as in Example 7) and the boosted preparation was compared to the EGII enriched preparation in biostoning of denim. The denim and test system for biostoning were as in Example 7, except for the temperature, which was 50° C. Also the effect of the cellulase treatment was evaluated as in Example 7. Enzyme preparations were dosed at 3–5 grams resulting in 0.22–0.38% on the weight of the fabric (Table 9).

Figure 4:
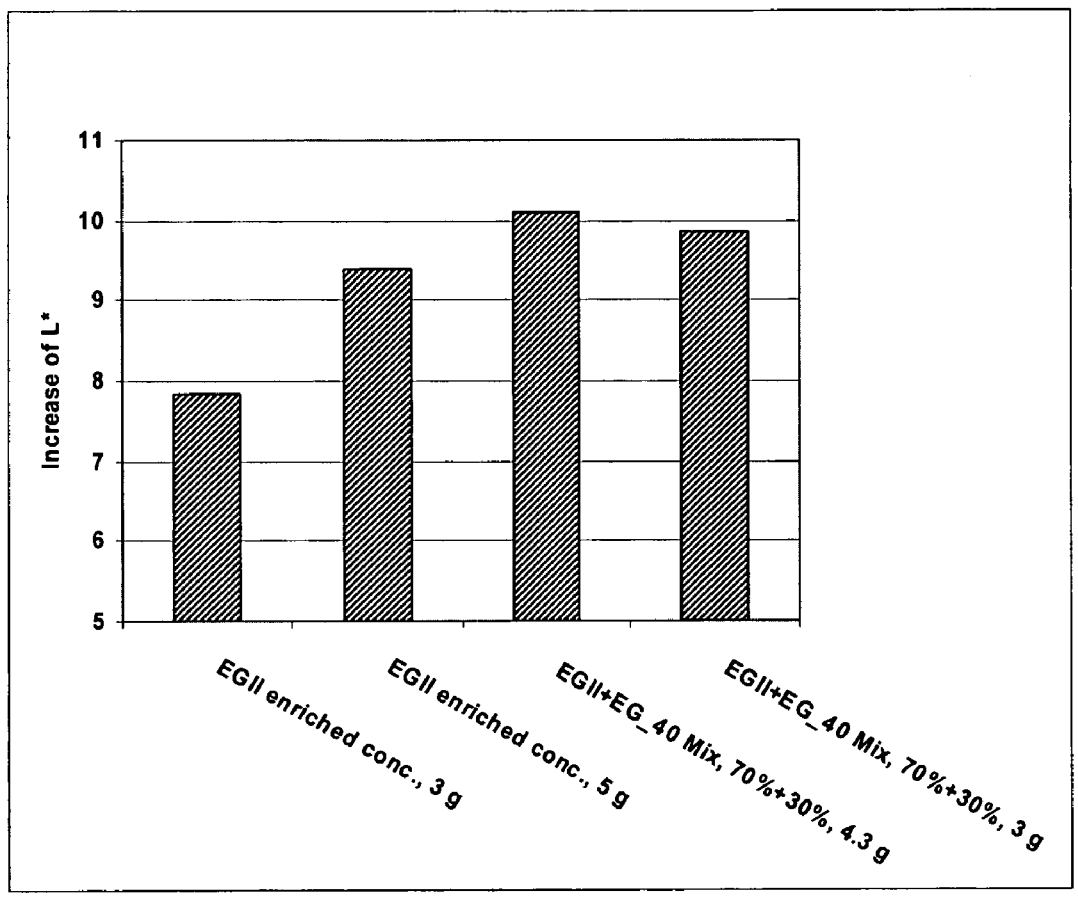
FIG. 4 shows the biostoning effect of a mixture of EGII-enriched concentrate and EG_40 concentrate as compared to the prior art EGII-enriched concentrate.

The results in Table 9 and FIG. 4 show that EG_40 can also be used to improve the abrasion effect of an EGII enriched preparation. With the EGII enriched preparation alone similar lightness levels to those obtained by the mixture containing 70% of the EGII enriched concentrate and 30% of EG_40 cellulase concentrate could not be obtained even with an increased dosage.

TABLE 9

Color measurements of the face side of denim treated at 50° C. with mixture of EGII enriched and EG_40 preparations compared to EGII enriched alone

| Enzyme preparation | Dosage, g | Dosage, % owf[a] | Before cellulase treatment L* | Before cellulase treatment b* | After cellulase treatment L* | After cellulase treatment b* | Increase of lightness |
|---|---|---|---|---|---|---|---|
| EGII enriched conc. | 5 | 0.38 | 22.32 | −15.47 | 31.72 | −17.50 | 9.40 |
| EGII enriched conc. | 3 | 0.23 | 22.24 | −15.57 | 30.08 | −17.64 | 7.84 |
| EGII + EG_40 mix. 70% + 30% | 4.3 | 0.33 | 22.20 | −15.53 | 32.31 | −17.46 | 10.11 |
| EGII + EG_40 mix 70% + 30% | 3 | 0.22 | 22.18 | −15.74 | 32.03 | −17.55 | 9.85 |

[a]on the weight of the fabric
[b]L* indicates the lightness, −b* is the blue direction, +b* is the yellow direction.

EXAMPLE 9

Performance of EG_40_like Cellulase Preparation in Denim Finishing

EG_40_like fermentation liquid from strain RF6071 and produced using *Trichoderma reesei* as host as described in Example 4 was compared to a EGII enriched concentrate in biostoning of denim. The denim and test system for biostoning were as in Example 7, except for the temperature, which was 60° C. and the amount of denim, which was leveled to 1430 g with an extra piece of different denim that was not included in the measurements. Also the effect of the cellulase treatment was evaluated as in Example 7.

The results in Table 10 show that the abrasion effect of EG_40_like was obtained with less back-staining (re-deposition of Indigo-dye) on the reverse side of denim. Especially the lightness of the pockets was higher and they were less blue.

TABLE 10

Color measurements of the face and reverse side of denim and pockets treated at 60° C. with EG_40_like preparation.

| Enzyme preparation | Dosage | Prot., mg/g fabric | Before cellulase treatment | | After cellulase treatment | | delta L* | delta b* |
|---|---|---|---|---|---|---|---|---|
| | | | L* | b* | L* | b* | | |
| Face side: | | | | | | | | |
| EG_40_like, RF6071 | 100 ml | 0.32 | 23.78 | −16.20 | 31.09 | −17.36 | 7.31 | −1.16 |
| EGII enriched | 1.5 g | 0.095 | 23.64 | −16.28 | 31.09 | −17.39 | 7.45 | −1.11 |
| Reverse side: | | | | | | | | |
| EG_40_like, RF6071 | 100 ml | 0.32 | 49.24 | −7.34 | 47.74 | −11.39 | −1.50 | −4.05 |
| EGII enriched | 1.5 g | 0.095 | 49.32 | −6.97 | 47.24 | −11.78 | −2.09 | −4.81 |
| Pockets: | | | | | | | | |
| EG_40_like, RF6071 | 100 ml | 0.32 | 75.42 | −8.78 | 66.39 | −13.20 | −9.03 | −4.42 |
| EGII enriched | 1.5 g | 0.095 | 76.63 | −7.95 | 64.41 | −13.91 | −12.22 | −5.96 |

Treatment with EGII enriched preparation was used for comparison. L* indicates the lightness, −b* is the blue direction, +b* is the yellow direction.

EXAMPLE 10

Performance of EG_40 and EGII Enriched Preparation Boosted with EG_40 in Biofinishing (Depilling)

The ability of the concentrated RF6118 EG_40 preparation and the ability of EGII enriched preparation boosted with EG_40 in depilling of cotton knitwear were compared to a commercial EGII enriched preparation, typically used in biofinishing formulations. The cellulase treatments were performed with Electrolux's Wascator FOM 71 CLS washer extractor under conditions described in Table 11.

Pieces of two kinds of low quality blue Polo-neck sweaters with fuzzy surface, made of 100% cotton jersey-based fabric or rib made of 95% cotton and 5% lycra, were used as test material with filling material. Samples were first pre-washed for 10 min at 60° C. with 1 ml/l surfactants/wetting agents (Sandoclean PCJ from Sandos and Imacol CN from Clariant) and rinsed 3 times. After this the cotton knits were treated with cellulase at 60° C. for 60 minutes in the presence of the same textile auxiliaries as used in pre-wash. The enzyme was inactivated as described in Example 7, except for the temperature which was 60° C. during the alkaline rinse, and the pieces of knitwear were rinsed three times and dried in the tumbler.

TABLE 11

The test conditions/process parameters used in biofinishing treatments.

| Process parameter | |
|---|---|
| Fabric load | 1.0 kg |
| Water | 15 liter |
| Sandoclean PCJ and Imacol CN | 1 ml/l |
| Buffer/pH control (pH 5–5.3) | ca. 3 ml Acetic acid (80%) |
| Time | 60 min |
| Temperature | 60° C. |

TABLE 11-continued

The test conditions/process parameters used in biofinishing treatments.

| Process parameter | |
|---|---|
| Cellulase dosage | 0.04% to 0.63% on the weight of the fabric |

The effect of the cellulase treatment was evaluated visually with a naked eye and with a loupe. Pre-washed sample without enzyme was used as control. The results are shown in Table 12.

The EG_40 preparation and the EGII enriched preparation boosted with EG_40 had excellent depilling properties compared to the commercial EGII enriched preparation that was used at dosing range typical for this enzyme concentrate in the biofinishing application. With the EG_40 preparation at least 8 times lower dosage and with the EGII enriched-EG_40 mixture at least 4 times lower dosages could be used than with EGII preparation to obtain similar effect.

The protein levels in the bioreactor culture supernatant are somewhat lower with the RF6118 strain than the *Trichoderma* producer strain of the EGII enriched preparation, when assayed with the used protein determination assay. In spite of this, the EG_40 culture medium is volumetrically at least 4–6 times more effective in biofinishing.

TABLE 12

The results of biofinishing treatments with EG_40 and EGII enriched preparations boosted with EG_40 compared to EGII enriched alone.

| Sample | Dosage g | Dosage, % owf[a] | Depilling effect[b] | Prot mg/g fabric |
|---|---|---|---|---|
| EGII enriched conc. | 6.3 | 0.63 | +++++ | 0.55 |
| EGII enriched conc. | 3.2 | 0.32 | +++ | 0.27 |
| EGII enriched + EG_40 mix. 70% + 13% | 3.2 | 0.32 | +++++ | 0.21 |
| EGII enriched + EG_40 mix. 70% + 13% | 1.6 | 0.16 | +++++ | 0.10 |
| EGII enriched + EG_40 mix. 70% + 13% | 0.8 | 0.08 | +++ | 0.052 |
| EG40 conc., RF6118 | 1.6 | 0.16 | +++++ | 0.050 |
| EG_40 conc., RF6118 | 0.8 | 0.08 | +++++ | 0.025 |
| EG_40 conc., RF6118 | 0.4 | 0.04 | +++ | 0.012 |
| Prewashed only, without enzyme | – | – | – | – |

[a] on the weight of the fabric
[b] +++++ Excellent depilling effect, visually very clean surface.
+++ Good depilling effect, visually relative clean surface.
– Dense surface fuzzing/and or severe pilling List of Deposited Organisms

| Strain | Plasmid contained | Deposition authority | Deposition date | Deposition number |
|---|---|---|---|---|
| Acremonium thermophilum ALKO4245 | — | CBS[1] | 20 Sep. 2004 | CBS 116240 |
| Escherichia coli | pALK1904 | DSMZ[2] | 13 May 2005 | DSM 17323 |
| Escherichia coli | pALK1908 | DSMZ | 13 May 2005 | DSM 17324 |

[1] the Centraalbureau Voor Schimmelcultures at Uppsalalaan 8, 3584 CT, Utrecht, the Netherlands
[2] Deutsche Sammlung von Mikroorganismen und Zellkulturen GmbH (DSMZ), Mascheroder Weg 1b, D-38124 Braunschweig, Germany

REFERENCES

Altschul S F, W Gish, W Miller, E W Myers and D J Lipman, (1990) "Basic local alignment search tool," *J. Mol. Biol.* 215:403–410.

Bailey M J and K M H Nevalainen, (1981) "Induction, isolation and testing of stable *Trichoderma reesei* mutants with improved production of solubilizing cellulose," *Enz. Microbiol. Technol.* 3:153–157.

Bendtsen J D, H Nielsen, G von Heijne and S Brunak, (2004) "Improved prediction of signal peptides: SignalP 3.0," *J. Mol. Biol.* 340:783–795.

Gasteiger, E, A Gattiker, C Hoogland, I Ivanyi, R D Appel and A Bairoch. (2003) "ExPASy: the proteomics server for in-depth protein knowledge and analysis," *Nucleic Acids Res.* 31:3784–3788.

Gupta, R., E. Jung and S. Brunak, (2004) "Prediction of N-glycosylation sites in human proteins, In preparation," www.cbs.dtu.dk/services/NetNGlyc/

Nierstrasz V. A. and Warmoeskerken M. M. C. G., (2003) "Process engineering and industrial enzyme applications," *Textile Processing with Enzymes*. A. Cavaco-Paulo and G. M. Gübitz (eds.) Woodhead Publishing Ltd, Cambridge. pp. 120–157.

Haakana H, A Miettinen-Oinonen, V Joutsjoki, A Mäntylä, P Suominen, and J Vehmaanperä, (2004) "Cloning of cellulase genes from *Melanocarpus albomyces* and their efficient expression in *Trichoderma reesei*," *Enz. Microbiol. Technol.* 34:159–167.

Henrissat B. (1991) "A classification of glycosyl hydrolases based on amino acid sequence similarities," *Biochem. J.* 280:309–316.

Henrissat B. and Bairoch A. (1993) "New families in the classification of glycosyl hydrolases based on amino acid sequence similarities," *Biochem. J.* 293:781–788.

Henrissat B. and Bairoch A. (1996) "Updating the sequence-based classification of glycosyl hydrolases," *Biochem. J.* 316:695–696.

IUPAC (International Union of Pure and Applied Chemistry) (1987) "Measurement of cellulase activities," *Pure and Appl. Chem.* 59:257–268.

Joutsjoki, W, T K Torkkeli and K M H Nevalainen (1993) "Transformation of *Trichoderma reesei* with the *Hormoconis resinae* glucoamylase P (gamP) gene: production of a heterologous glucoamylase by *Trichoderma reesei*," *Curr. Genet.* 24:223–228.

Karhunen T, A Mäntylä, K M H Nevalainen and P L Suominen (1993) "High frequency one-step gene replacement in *Trichoderma reesei*. I. Endoglucanase I overproduction," *Mol. Gen. Genet* 241:515–522.

Lowry O H, N J Roseborough, A L Farr and R J Randall (1951) "Protein measurement with the Folin phenol reagent," *J. Biol Chem* 193:265–275.

Malardier L, Daboussi M J, Julien J, Roussel F, Scazzocchio C and Brygoo Y. (1989) "Cloning of the nitrate reductase gene (niaD) of *Aspergillus nidulans* and its use for transformation of *Fusarium oxysporum*," *Gene* 15:147–156.

Needleman S. and Wunsch C. (1970) "A general method applicable to the search for similarities in the amino acid sequence of two proteins," *Journal of Molecular Biology* 48, 443–453.

Nielsen H., J. Engelbrecht, S. Brunak, and G. von Heijne (1997) "Identification of prokaryotic and eukaryotic signal peptides and prediction of their cleavage sites," *Prot. Engineering* 10:1–6.

Nierstrasz V. A. and Warmoeskerken M. M. C. G. (2003) "Process engineering and industrial enzyme applications," *Textile Processing with Enzymes*. A. Cavaco-Paulo and G. M. Gübitz (eds.) Woodhead Publishing Ltd, Cambridge. pp. 120–157.

Paloheimo M, A Mäntylä, J Kallio, and P Suominen (2003) "High-yield production of a bacterial xylanase in the filamentous fungus *Trichoderma reesei* requires a carrier polypeptide with an intact domain structure," *Appl. Env. Microbiol.* 69:7073–7082.

Penttilä M, H Nevalainen, M Rättö, E Salminen and J Knowles (1987) "A versatile transformation system for the cellulolytic filamentous fungus *Trichoderma reesei*," *Gene* 61:155–164.

Raeder U and P Broda (1985) "Rapid preparation of DNA from filamentous fungi," *Lett. Appl. Microbiol.* 1:17–20.

Rice P, Longden I and Bleasby A. (2000) "EMBOSS: The European Molecular Biology Open Software Suite," *Trends in Genetics* 16:276–277.

Sambrook J, E F Fritsch and T Maniatis (1989) *Molecular Cloning, a Laboratory Manual*, Cold Spring Harbor Laboratory, New York, U.S.

Sambrook J and D W Russell. 2001. *Molecular Cloning, a Laboratory Manual*, Cold Spring Harbor Laboratory, New York, U.S.

Ward M, Shan W, Dauberman J, Weiss G, Larenas E, Bower B, Rey M, Clarkson K and Bott R. (1993) "Cloning, sequence and preliminary structural analysis of a small, high pI endoglucanase (EGIII) from *Tricho-*

*derma reesei*," Proceedings of the second TRICEL symposium on TRICHODERMA REESEI CELLULASES AND OTHER HYDROLASES, Espoo, Finland, 1993, ed. by P. Suominen and T. Reinikainen. Foundation for Biotechnical and Industrial Fermentation Research 8 (1993):153–158.

---

The invention claimed is:

1. A recombinant endoglucanase polypeptide comprising a fragment having cellulolytic activity and being selected from the group consisting of:
   a) a polypeptide comprising an amino acid sequence having at least 90% sequence identity to the amino acid sequence of SEQ ID NO: 2; and
   (b) a fragment of a) having cellulolytic activity.

2. The recombinant endoglucanase polypeptide of claim 1, wherein said polypeptide has the amino acid sequence of SEQ ID NO: 2.

3. The recombinant endoglucanase polypeptide of claim 1, which is obtainable or originates from an *Acremonium* sp.

4. The recombinant endoglucanase polypeptide of claim 3, wherein the *Acremonium* sp. is CBS 116240.

5. A process for the production of the recombinant endoglucanase polypeptide of claim 1 comprising the step of culturing a host cell comprising a polynucleotide sequence encoding the recombinant endoglucanase polypeptide comprising a fragment having cellulolytic activity and being selected from the group consisting of:
   a) a polypeptide comprising an amino acid sequence having at least 90% sequence identity to the amino acid sequence of SEQ ID NO: 2; and
   b) a fragment of a) having cellulolytic activity.

6. An enzyme preparation comprising the recombinant endoglucanase polypeptide of claim 1.

7. A process for biostoning which comprises the step of adding the endoglucanase polypeptide of claim 1 to cotton-containing fabric or garments.

8. A process for biofinishing, which comprises the step of adding the endoglucanase polypeptide of claim 1 to textile materials.

9. A detergent composition comprising the recombinant endoglucanase polypeptide of claim 1 and an auxiliary selected from the group consisting of surface active agents, surfactants, bleaching agents and builders.

10. A method of treating cellulosic fiber containing textile material, wherein said method comprises contacting said textile material with the detergent composition of claim 9.

11. A method for treating wood-derived pulp or fiber, which comprises the step of adding the endoglucanase polypeptide of claim 1 to wood-derived mechanical or chemical pulp or secondary fiber.

12. A method for improving the quality of animal feed, which comprises treating plant material with the endoglucanase polypeptide of claim 1.

13. The recombinant endoglucanase polypeptide of claim 1, wherein said polypeptide has at least 95% sequence identity to the amino acid sequence of SEQ ID NO: 2.

14. The recombinant endoglucanase polypeptide of claim 1, wherein said polypeptide has at least 98% sequence identity to the amino acid sequence of SEQ ID NO: 2.

15. The recombinant endoglucanase polypeptide of claim 1, which is obtainable or originates from *Acremonium thermophilum*.

16. A process for biostoning which comprises applying the preparation of claim 6 to cotton-containing fabrics or garments.

17. A process for biofinishing, which comprises applying the preparation of claim 6 to a textile material selected from the group consisting of fabrics, garments, and yarn.

18. A detergent composition comprising the preparation of claim 6 and an auxiliary selected from the group consisting of surface active agents, surfactants, bleaching agents and builders.

19. A method for treating wood-derived pulp or fiber, which comprises the step of applying the preparation of claim 6 to wood-derived mechanical or chemical pulp or secondary fiber.

20. A method for improving the quality of animal feed, which comprises adding the preparation of claim 6 to the animal feed.

21. The process for biostoning of claim 16, wherein the cotton-containing fabrics or garments are denim.

* * * * *